(12) United States Patent
Lee et al.

(10) Patent No.: US 10,350,400 B2
(45) Date of Patent: Jul. 16, 2019

(54) APPARATUS AND METHODS FOR ASEPTIC FLUID INTERCONNECTS

(71) Applicant: Pharyx, Inc., Woburn, MA (US)

(72) Inventors: Harry Lee, Malden, MA (US); Kevin Lee, Cambridge, MA (US)

(73) Assignee: ERBI BIOSYSTEMS, INC., Woburn, MA (US)

( * ) Notice: Subject to any disclaimer, the term of this patent is extended or adjusted under 35 U.S.C. 154(b) by 221 days.

(21) Appl. No.: 15/268,616

(22) Filed: Sep. 18, 2016

(65) Prior Publication Data

US 2017/0080201 A1 Mar. 23, 2017

Related U.S. Application Data

(60) Provisional application No. 62/221,044, filed on Sep. 20, 2015.

(51) Int. Cl.
| | |
|---|---|
| *A61M 39/10* | (2006.01) |
| *A61M 39/12* | (2006.01) |
| *A61M 39/16* | (2006.01) |
| *A61M 39/18* | (2006.01) |
| *A61M 39/22* | (2006.01) |
| *F04B 43/12* | (2006.01) |

(52) U.S. Cl.
CPC ...... *A61M 39/1011* (2013.01); *A61M 39/105* (2013.01); *A61M 39/12* (2013.01); *A61M 39/16* (2013.01); *A61M 39/18* (2013.01); *A61M 39/22* (2013.01); *F04B 43/12* (2013.01)

(58) Field of Classification Search
CPC ............ A61M 39/1011; A61M 39/105; A61M 39/12; A61M 39/16; A61M 39/18; A61M 39/22; F16L 2201/44; Y10S 604/905
See application file for complete search history.

(56) References Cited

U.S. PATENT DOCUMENTS

| | | | | |
|---|---|---|---|---|
| 3,865,411 | A | 2/1975 | Rowe | |
| 4,418,945 | A * | 12/1983 | Kellogg | A61M 39/14 285/423 |
| 4,473,369 | A * | 9/1984 | Lueders | A61M 39/1011 285/419 |
| 4,630,847 | A | 12/1986 | Blenkush | |
| 5,015,013 | A * | 5/1991 | Nadin | F16L 25/0045 285/419 |
| 5,088,515 | A * | 2/1992 | Kamen | A61M 39/22 137/15.17 |
| 5,478,119 | A | 12/1995 | Dye | |
| 6,679,529 | B2 | 1/2004 | Johnson | |

(Continued)

OTHER PUBLICATIONS

Bonded Dictionary Definition (Keyword Search Bonded). https://www.google.com/. (Year: 2019).*

*Primary Examiner* — Tyrone V Hall, Jr.
(74) *Attorney, Agent, or Firm* — May Ming Wu

(57) ABSTRACT

The present invention provides apparatus and methods for making multiple aseptic fluid interconnections in parallel with an integral clamping mechanism and elastomeric fluid sealing gasket to provide an initial fluid tight seal while removing sealing tape tabs and a final fluid tight seal after sealing tape tabs are removed. The clamping mechanism comprises a hinge coupling and a first set of snap-fit locks to maintain the initial fluid tight seal and a second set of snap-fit locks to maintain the final fluid tight seal.

6 Claims, 16 Drawing Sheets

(56) References Cited

U.S. PATENT DOCUMENTS

| | | |
|---|---|---|
| 7,523,918 B2 | 4/2009 | Matkovich |
| 8,491,016 B2 | 7/2013 | Williams |
| 8,596,326 B2 * | 12/2013 | Loy ..................... A61M 39/14 156/247 |
| 2003/0030272 A1 * | 2/2003 | Johnson ................ A61M 39/18 285/3 |
| 2013/0048111 A1 | 2/2013 | Gebauer |
| 2013/0196276 A1 | 8/2013 | Lee |
| 2015/0061282 A1 * | 3/2015 | Faldt .................... A61M 39/18 285/124.5 |

* cited by examiner

FIG 5
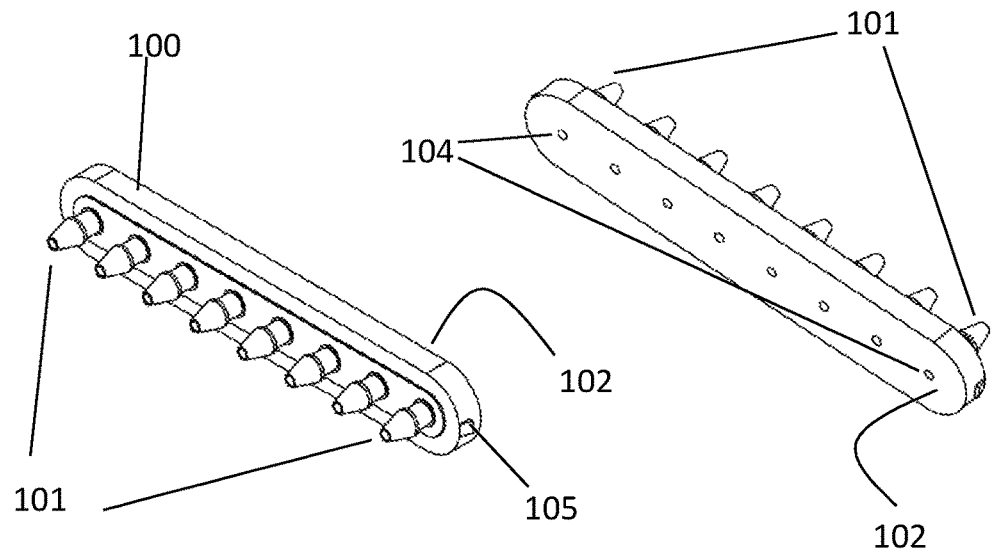
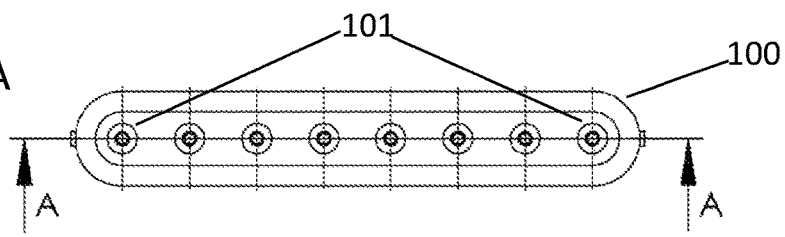
FIG 6A
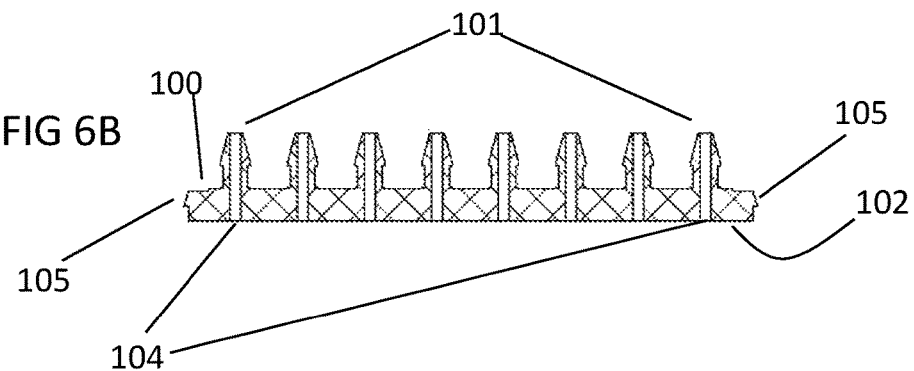
FIG 6B

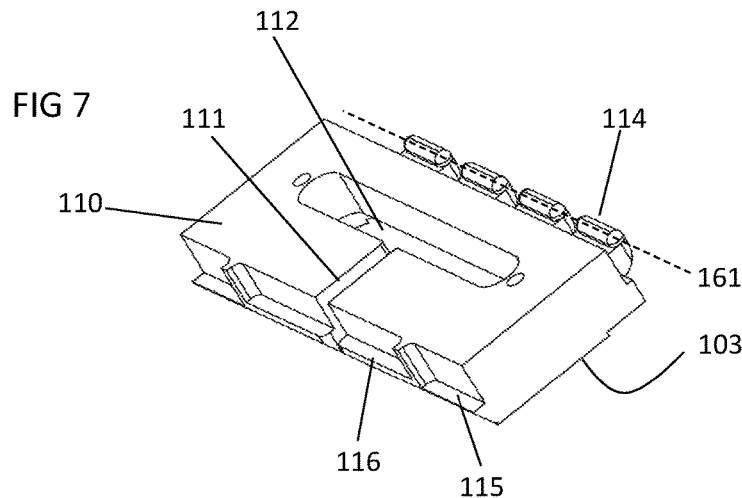
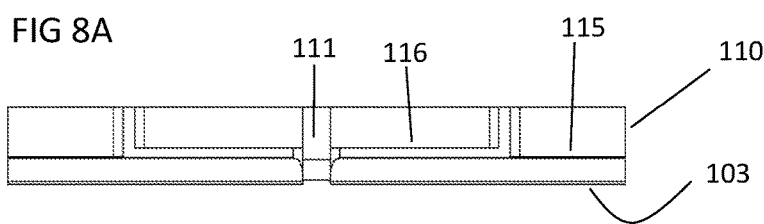
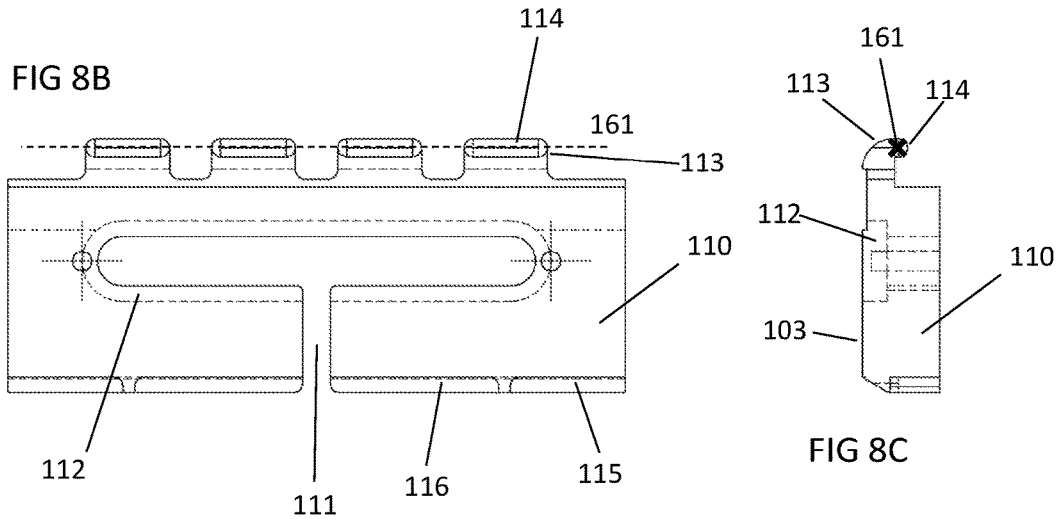

APPARATUS AND METHODS FOR ASEPTIC FLUID INTERCONNECTS

RELATED APPLICATIONS

This application claims priority from U.S. Provisional Application 62/221,044, entitled "Apparatus and methods for aseptic fluid interconnects", filed Sep. 20, 2015, the content of which is hereby incorporated by reference in its entirety.

TECHNICAL FIELD

The field of the invention relates to fluid interconnections.

BACKGROUND OF THE INVENTION

All referenced patents and applications and publications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

Aseptic fluid connectors are necessary for conveniently making fluid connections between systems without contaminating the inside of the system with microorganisms. Uses include making sterile connections for biomedical applications, and making sterile connections for bioprocessing applications. With the growing adoption of single use bioprocessing systems, a number of aseptic fluid connectors have reached the market place such as the GE ReadyMate series (U.S. Pat. No. 6,679,529), the Pall Kleenpack series (U.S. Pat. No. 7,523,918), and the Colder Aseptiquik series (U.S. Pat. No. 8,491,016). Commercially available aseptic connectors are typically for a single aseptic connection and do not solve the problem of rapidly making many aseptic connections in parallel. Typically, many single aseptic connectors are used and many single aseptic connections are made one by one.

One scenario where many connections are required is the interconnection of one or more microfluidic devices to fluid sources or receptacles. For example, a single microfluidic bioreactor can require 8 aseptic fluid interconnections and connecting a system of four such microfluidic bioreactors would require 32 aseptic fluid interconnections.

In addition to the inefficiency of manually operating individual aseptic fluid interconnects, the physical size of the large number of aseptic fluid interconnects is undesirable. The size of the aseptic fluid interconnects significantly increases the overall size of the microfluidic device packaging, and also increases the footprint of the complete microfluidic system.

U.S. patent application Ser. No. 13/750,982 discloses apparatus and methods for making aseptic connections between a set of bottles and a microbioreactor device. The apparatus comprises a fluid interface with conduits having openings on a planar surface of the fluid interface that correspond to openings in the microbioreactor device, a gasket sealed to the planar surface of the fluid interface, where the gasket has openings corresponding to the conduit openings. A first sealing tape tab protects the gasket and corresponding fluid interface from contamination, and a second sealing tape tab protects the microbioreactor device from contamination. To make the aseptic connection, the tape tabs are folded over themselves and the microbioreactor device is aligned to the fluid interface gasket with alignment features. Using manual pressure, the tape tabs are brought into contact and pressed together. While continuing to apply pressure the tape tabs are pulled out, exposing the aseptic surfaces protected by the tape and allowing them to contact. The manual pressure applied provides the initial seal, and the final seal is made by applying a spring clamp to seal the microbioreactor device onto the fluid interface gasket.

While this system does enable many aseptic connections to be made in parallel in a small form factor, it is prone to operator error due to the manual pressure required to form the initial seal while the tape tabs are pulled, and the degree of manual dexterity required to apply the final spring clamp while maintaining the initial manual seal.

patent application Ser. No. 14/385,307 discloses a multi-port aseptic connector, however it requires two different sealing materials, a fluid tight gasket, and a compressible foam in order to make an aseptic connection. In addition, this connector requires a separate clamp in order to make the final connection, which is inconvenient when a large number of connections need to be made.

Thus, there remains a considerable need for easy to use and easy to manufacture apparatus to perform rapid, multi-port, aseptic fluid interconnects in a compact form factor.

SUMMARY OF INVENTION

The present invention relates to apparatus and methods to make multiple aseptic connections in parallel in a compact form factor.

In particular, we consider apparatus and methods for making multiple aseptic fluid interconnections in parallel with an integral clamping mechanism and an elastomeric fluid sealing gasket that provide an initial fluid tight seal while removing sealing tape tabs and a final fluid tight seal after sealing tape tabs are removed. Among the many different possibilities contemplated, the clamping mechanism comprises a hinge coupling and a first set of snap-fit locks to maintain the initial fluid tight seal and a second set of snap-fit locks to maintain the final fluid tight seal.

It is further contemplated that the apparatus comprises a first tubing carrier 100 having a set of tubing ports 101 to connect a first set of tubing to a first set of openings on a first gasket sealing surface 102; a first sealing tape tab 120 sealed to the first gasket sealing surface 102 to protect the first gasket sealing surface 102 from contamination; a second tubing carrier 200 having a set of tubing ports 201 to connect a second set of tubing to a second set of openings on a second gasket sealing surface 202, where the first set of openings correspond to the second set of openings when the first and second gasket sealing surfaces are positioned to face each other; a fluid sealing gasket 300 having openings corresponding to the second set of openings; a second sealing tape tab 220 sealed to gasket openings 304 to protect the gasket openings 304 from contamination; a clamping structure comprising a first 110 and second tubing carrier locking body 210; a hinge coupling 160 between the two locking bodies, 110 and 210 such that the two locking bodies pivot along the hinge coupling axis 161 between an open position, an initial sealing position, and a final sealing position, where in the open position the fluid sealing gasket 300 is not compressed, in the initial sealing position the fluid sealing gasket 300 is in a first state of compression such that there is a low pressure fluid tight seal between the first tubing ports 101 and second tubing ports 201, and in the final sealing position the fluid sealing gasket 300 is further compressed in a second state of compression such that there is a high pressure fluid tight seal between the first tubing ports 101 and second tubing ports 201; a first retaining structure 115 with 215 that constrains the locking bodies 110 and 210 from moving from the initial sealing position to the open position; a second retaining structure 116 with 216 that constrains the locking bodies 110 and 210 in the final sealing position.

A method for operating the apparatus comprises the steps of ensuring the first tape tab 120 is folded over itself; ensuring the second tape tab 120 is folded over itself; engaging the hinge coupling between the first 110 and second 210 tubing carrier locking; positioning the locking bodies in the initial sealing position where the locking bodies are retained by the first retaining structure; pulling the first 120 and second tape tabs 220 out to expose the previously sealed first gasket sealing surface 102 and gasket openings 304; positioning the locking bodies in the final sealing position where the locking bodies are retained by the second retaining structure.

It is further contemplated that the fluid sealing gasket 300 may be bonded to the gasket sealing side of the second tubing carrier 200, or that the second tubing carrier 200 further comprises a gasket retention pocket 206 optionally having gasket expansion regions 207 and the fluid sealing gasket 300 may or may not be bonded to the gasket retention pocket 206. For the case where the fluid sealing gasket 300 is not bonded to the gasket retention pocket 206, the second sealing tape 220 would seal against the tape sealing surface 203 of the second tubing carrier 200, and protect the entire fluid sealing gasket 300 from contamination.

It is further contemplated that the hinge coupling comprises a first half integral to the first tubing carrier locking body and a second half integral to the second tubing carrier locking body, where the first half of the hinge locking body comprises a set of claws 113, and the second half of the hinge locking body comprises a set of sockets 213.

It is further contemplated that the first tubing carrier and first tubing carrier locking body are integral, and/or the second tubing carrier and second tubing carrier locking body are integral.

It is further contemplated that the first retaining structure comprises a first snap-fit locking tab 215 integral to the second tubing carrier locking body 210, where in the initial sealing position, the first snap-fit locking tab 215 is engaged to a first snap-fit tab ledge 115 on the first tubing carrier locking body 110; and the second retaining structure comprises a second snap-fit locking tab 216 integral to the second tubing carrier locking body 210, where in the final sealing position, the second snap-fit locking tab 216 is engaged to a second snap-fit tab ledge 116 on the first tubing carrier locking body 110 and the first snap-fit locking tab 215 is no longer engaged to the first snap-fit tab ledge 115 on the first tubing carrier locking body 110.

It is further contemplated that a tape retention structure 400 is used to maintain the seal of the second tape tab 220 to the second tubing carrier 200 during sterilization and storage of the aseptic connector apparatus.

It is further contemplated that the apparatus may be advantageously used to aseptically connect microfluidic devices to external fluid sources when maintaining sterility is important such as for cell culture devices or biomedical devices. In this application, each half of the aseptic connector would be sterilized and then aseptic connections between the tubing on each half of the aseptic connector would be made using the aseptic connector apparatus.

Various features and aspects of the present invention will become more apparent from the following detailed description of preferred embodiments of the invention, along with the accompanying drawings in which like numerals represent like components.

BRIEF DESCRIPTION OF THE DRAWING

The embodiments of the present invention will now be described by reference to the following figures, in which:

FIG. 5 shows two isometric views of a first tubing carrier 100, each view oriented approximately 180 degrees about the long axis of the part.

FIG. 6A shows a top view of FIG. 5.

FIG. 6B shows a section view of FIG. 6A along the line A-A.

FIG. 7 is an isometric view of a first tubing carrier locking body 110.

FIG. 8A shows rear edge view of a first tubing carrier locking body 110.

FIG. 8B shows a top view of a first tubing carrier locking body 110.

FIG. 8C shows a side view of a first tubing carrier locking body 110.

DETAILED DESCRIPTION OF THE DRAWING

Figure 1:
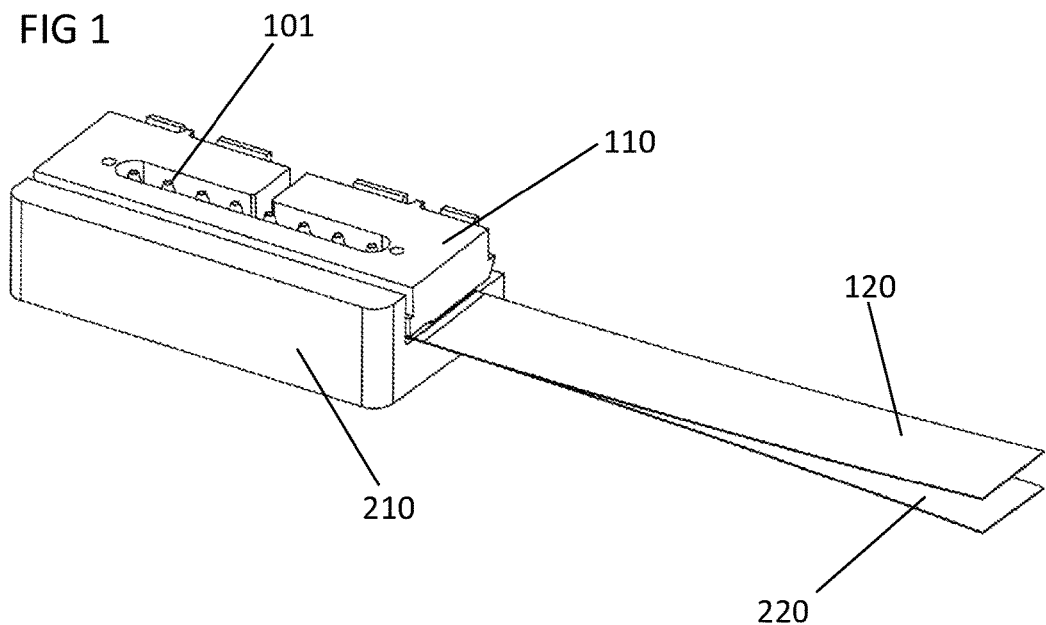
FIG. 1 is a top-side isometric view of an embodiment shown in an initial sealing position.
Figure 2:
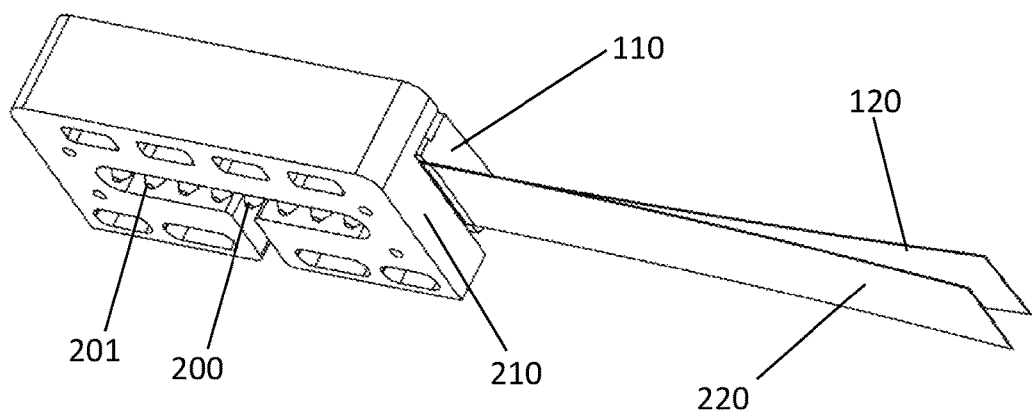
FIG. 2 is a bottom-side isometric view of an embodiment shown in an initial sealing position.

FIG. 1 is a top-side isometric view and FIG. 2 is a bottom-side isometric view of an aseptic fluid connector embodiment shown in an initial sealing position. The aseptic fluid connector embodiment comprises a first tubing carrier 100, a first tubing carrier locking body 110, a second tubing carrier 200, a second tubing carrier locking body 210, a first sealing tape tab 120, a second sealing tape tab 220.

Figure 3:
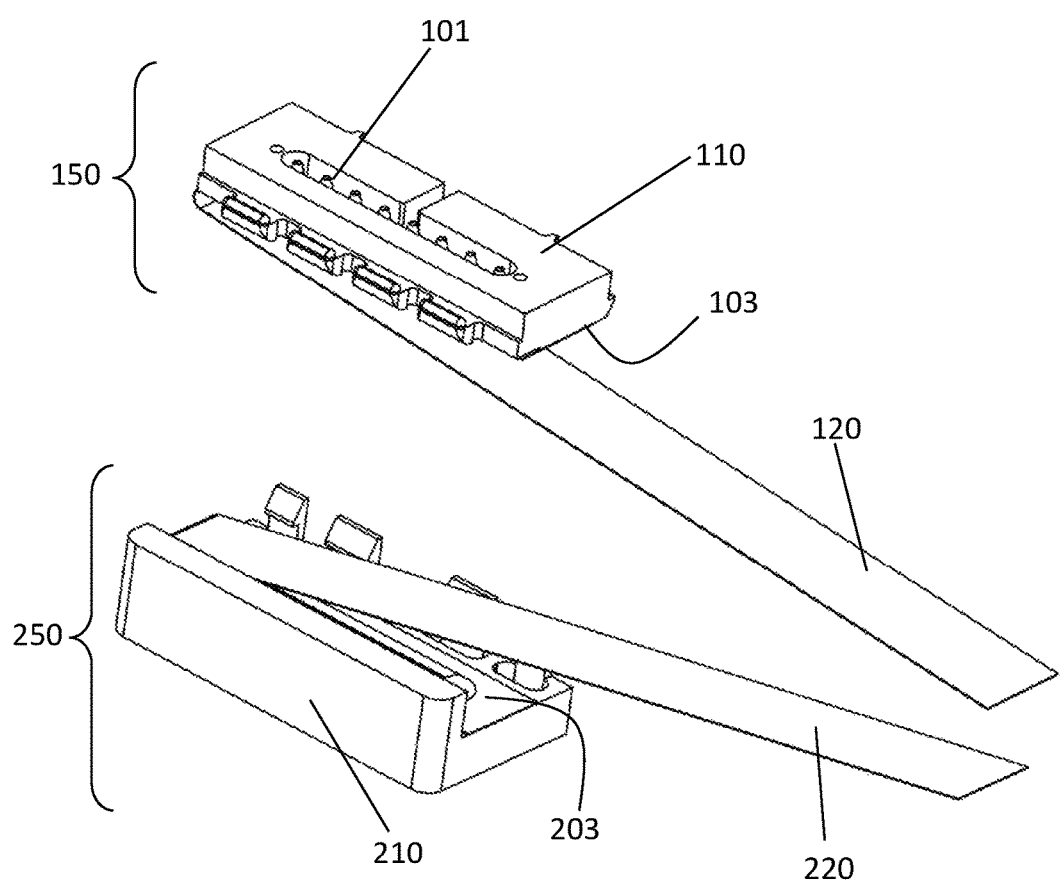
FIG. 3 is a partial exploded view of FIG. 1 showing two separated tubing carriers.

FIG. 3 shows a partially exploded view of the embodiment shown in FIG. 1 where the first half 150 of the aseptic fluid connector embodiment is separated from the second half 250 of the aseptic fluid connector embodiment. As part of an aseptic fluid system, tubing was connected to the first tubing carrier 100 using eight individual tubing ports 101 of the first tubing carrier 100. The first sealing tape tab 120 was sealed to the opposite side of the tubing ports 101 on the gasket sealing surface 102 of the first tubing carrier 100. The opposite ends of the tubing were connected to a device such as a microfluidic device, a bioreactor, a peristaltic pump, or other device which requires sterile connections. The entire assembly of the first half 150 of the aseptic fluid connector embodiment, tubing, and device was then sterilized with gamma irradiation, although it is known in the art that steam autoclave, dry heat, ethylene oxide gas, or other sterilization method can also be used. Similarly, referring to FIG. 2 and FIG. 3, tubing was connected to the second tubing carrier 200, using eight individual tubing ports 201 of the second tubing carrier 200. The second sealing tape tab 220 was then sealed to opposite side of the tubing ports 201 on the tape sealing surface 203 of the second tubing carrier 200. The opposite ends of the tubing were connected to fluid sources or fluid delivery systems such as single use bioprocess container bags, iv bags, fluid bottles, air compressors, peristaltic pumps, or other delivery systems, and the entire assembly of the second half 250 of the aseptic fluid connector embodiment, tubing, and fluid sources were sterilized with gamma irradiation, although it is known in the art that steam autoclave, dry heat, ethylene oxide gas, or other sterilization method can also be used.

Figure 4:
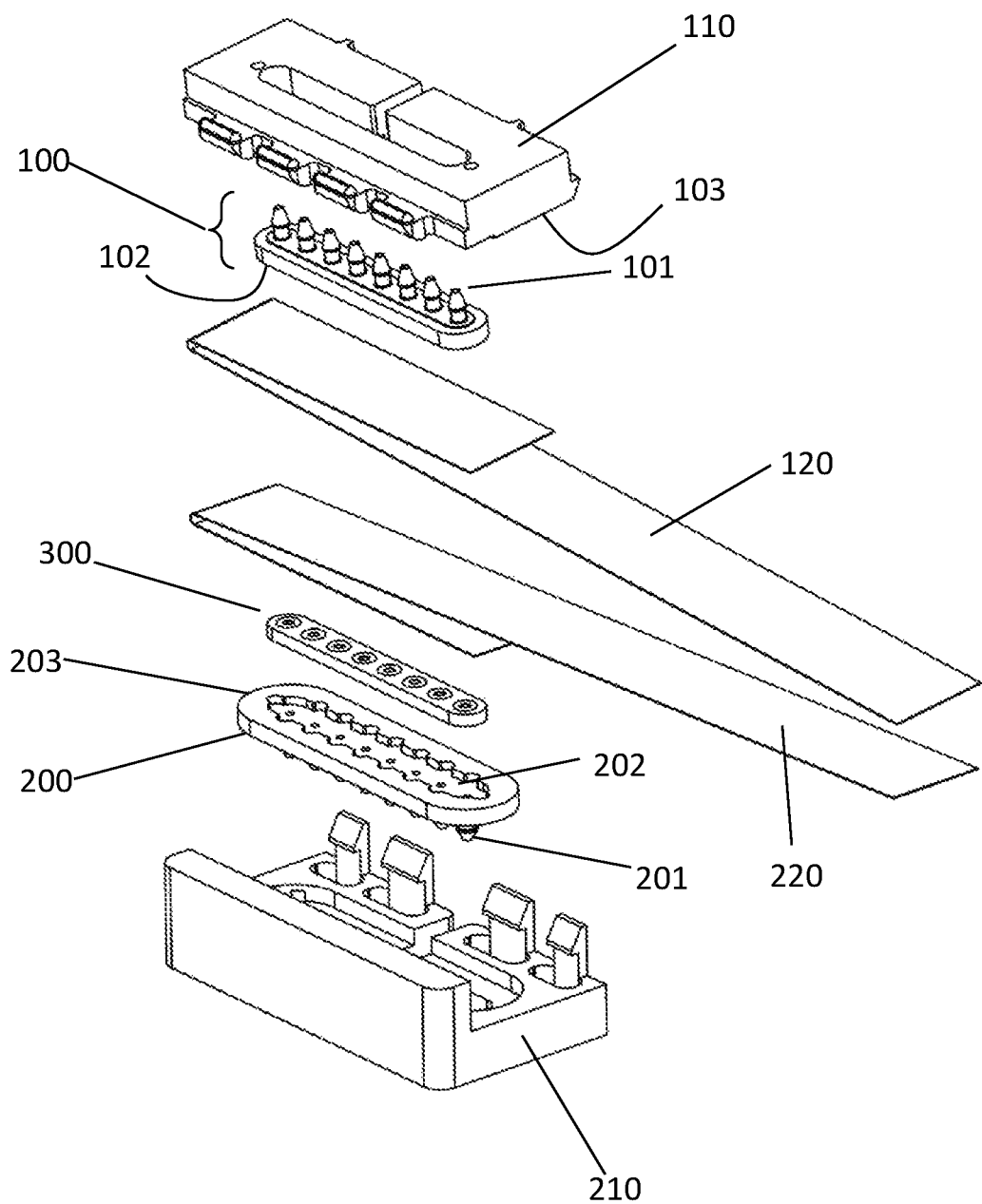
FIG. 4 fully exploded view of FIG. 1.

FIG. 4 shows an exploded view of an aseptic fluid connector embodiment which shows the first tubing carrier 100 separated from the first tubing carrier locking body 110. Also shown is a fluid sealing gasket 300 and the second tubing carrier 200 separated from the second tubing carrier locking body 210. The first sealing tape tab 120 and the second sealing tape tab 220 comprised a strip of polyester tape approximately 9 inches long, 0.5 inches wide, and 0.003 inches thick, with silicone adhesive. At one end, two inches of adhesive was exposed while the remaining approximately 7 inches was covered by a 0.0005 inch thick polyester film to render that portion of the tape non-sticky and form a pull tab. The end of the first sealing tape tab 120 was sealed to the gasket sealing surface 102 of the first tubing carrier and the adjacent bottom surface 103 of the first tubing carrier locking body 110 to prevent contamination of the first gasket sealing surface and subsequently the tubing ports 101 of the first tubing carrier 100. It is known in the art that other methods of aseptic sealing may be used such as different varieties of tape, different means to render the tape non-sticky to form a pull tab, such as removing the adhesive with solvent, using alternative cover film materials such as paper, or polyethylene, or other materials, or forming a pull tab with a non adhesive strip adhered to a shorter length of adhesive tape are possible. Other alternatives are to not use an adhesive at all and to use heat sealing or other sealing method to seal a plastic strip to the first gasket sealing surface or the tape sealing surface. In addition, it should be clear to one of ordinary skill that a wide range of tape dimensions may be used, such as tapes from 0.0005 inches thick to 0.010 inches thick or other thicknesses, tapes with width from 0.25 inches to 0.75 inches wide, or other widths, and tapes with length from 5 inches to 15 inches, or other lengths FIG. 5 shows two isometric views of the first tubing carrier 100 comprised of a set of tubing ports 101 suitable for attaching tubing such that the interior of each tube is fluidically connected to the openings 104 of the tubing ports on the gasket sealing surface 102 of the first tubing carrier 100.

FIG. 6A shows a top view of the first tubing carrier 100 and FIG. 6B shows a section view along the line A-A in FIG. 6A. The cross section shows the fluidic connection between the fluid ports 101 and the openings 104 on the gasket sealing surface 102 of the first tubing carrier 100. Two small locking tabs 105 were located at the edges of the first tubing carrier locking body. These locking tabs interfaced with the first tubing carrier locking body 110 to hold the first tubing carrier 100 in place.

In further detail referring to FIGS. 5, 6A, and 6B, the first tubing carrier was fabricated by CNC machining 0.236 inch thick polycarbonate sheet stock to form the shape depicted in FIG. 5. The overall length was approximately 1.5 inches long and the width was approximately 0.25 inches wide. The tubing ports 101 were fabricated as tubing barbs were approximately 0.150 inches long, 0.080 inches in diameter at the widest point and an approximately 30 degree taper. The tubing ports 101 were barbs suitable for attaching tubing with 1/32 inch inner diameter and 3/32 inch outer diameter. Other size barbs were also contemplated such as barbs suitable for tubing with 1/16 inch inner diameter and 1/8 inch outer diameter, and also other size barbs for other size tubing. Eight tubing ports were fabricated, although it should be understood that any number of tubing ports could be used. It should be noted that other fabrication methods may be used such as injection molding, 3D-printing, or other fabrication method. It should also be noted that the style of tubing port may vary, including cylindrical or other shaped tubing ports. It should also be noted that the overall dimensions may vary. It should also be noted that other materials may be used such as acrylic, polypropylene, cyclic-polyolefin-copolymer, or other plastic, metal, or other material may be used.

FIG. 7 shows an isometric view and FIGS. 8A, 8B, and 8C show rear, top and side views of the first tubing carrier locking body 110 which comprised a slot pocket 112 to mount the first tubing carrier 100 such that the gasket sealing surface 102 of the first tubing carrier was approximately flush with the bottom surface 103 of the first tubing carrier locking body 110. A first tubing slot 111 enabled insertion of the first tubing carrier 100 into the first tubing carrier locking body 110 after tubing had been attached to the first tubing carrier 100. This was advantageous because it allows easier access to the tubing port 101 barbs while attaching the tubing. In addition, separating the first tubing carrier 100 and the first tubing carrier locking body 110 facilitated the fabrication of both parts. In particular both the first tubing carrier and the first tubing carrier locking body are able to be fabricated with injection molding.

Referring to FIGS. 7, 8A, 8B, and 8C in more detail, the first tubing carrier locking body 110 further comprised a hinge claw 113. When the hinge claw 113 was constrained by a hinge pocket 213 (See FIG. 12 and FIG. 14) the motion of the first tubing carrier locking body was constrained to approximately pivot about the hinge coupling axis 161, indicated by the dashed line in FIG. 8B and the X in FIG. 8C, of the hinge claw 113, which was the axis along the center of curvature of the upper cylindrical tip 114 of the hinge claw 113.

Referring to 7, 8A, 8B, and 8C in even more detail, the first tubing carrier locking body 110 further comprised a first snap-fit tab ledge 115 and a second snap-fit tab ledge 116. The distance between the first snap-fit tab ledge 115 and the bottom surface 113 of the first tubing carrier locking body 110 was less than the distance between the second snap-fit tab ledge 116 and the bottom surface 113 of the first tubing carrier locking body 110. These snap-fit tab ledges were regions where the overhang of a snap-fit tab 215, 216 (See FIGS. 12, 13, 14) would engage, thereby preventing the first tubing carrier locking body from pivoting against the snap-fit tab 215, 216 overhang. It should be noted that the distances between the snap fit tab ledges 115, and 116 and the bottom surface 113 should be chosen in conjunction with the shape of the snap fit tabs 215 and 216 to achieve the desired function of an initial sealing position and a final sealing position. It should be clear to those of ordinary skill in the art that there are many ways to do this and the inventive concept is not limited to the specific structures illustrated here.

Referring to FIGS. 7, 8A, 8B, and 8C in still more detail, the first tubing carrier locking body 110 was fabricated by CNC machining a 0.236 inch thick polycarbonate sheet stock. The length of a preferred embodiment of the first tubing carrier locking body was 2.0 inches, and the width 0.82 inches. It should be clear to one of ordinary skill in the art that the part could be fabricated using other materials, such as other thermoplastics, or metals, and also using other fabrication methods such as injection molding or 3D printing, or other fabrication methods.

Figure 9:
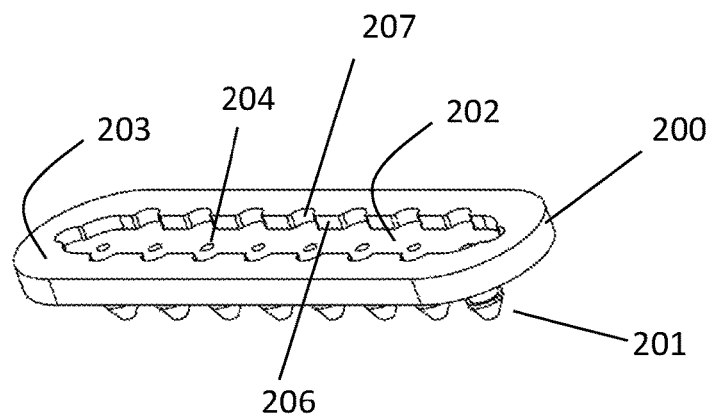
FIG. 9 shows an isometric view of a second tubing carrier 200.

FIG. 9 shows an isometric view of the second tubing carrier 200 comprised of a set of tubing ports 201 suitable for attaching tubing such that the interior of each tube was fluidically connected to the openings 204 of the tubing ports on the gasket sealing surface 202 of the second tubing carrier 200. The second tubing carrier further comprised a tape sealing surface 203, which was sealed by the second sealing tape tab 220, and a gasket pocket 206. The gasket pocket 206 was a recessed region that partially captured the fluid sealing gasket 300, where the bottom surface of the gasket pocket 206 was the second gasket sealing surface 202. The depth of the gasket pocket 206 was less than the thickness of the fluid sealing gasket 300 such that the top of the gasket was higher than the tape sealing surface 203 when the fluid sealing gasket 300 was placed in the gasket pocket 206. The gasket pocket 206 had cut out features 207 around the perimeter to provide empty space for the gasket to deform when compressed so as not to close off the gasket holes. The second sealing tape tab 220 was sealed over the entire fluid sealing gasket 300 on the tape sealing surface 203. This protected the entire fluid sealing gasket 300 and second gasket sealing surface 202 from contamination. It should be noted that there are other geometries contemplated, such as configurations without a gasket pocket 206, where the fluid sealing gasket 300 is bonded directly to the second gasket sealing surface 202, and where the second gasket sealing surface 202 is flush with the tape sealing surface 203. It should be noted that the design objective is to prevent contamination of the second tubing ports 201 such that an aseptic connection can be made with the first tubing ports 101. As such, other geometries would be suitable for this purpose, such as eliminating the gasket pocket 206 and using a large gasket covering the entire area of the second tubing carrier and bonded to the second tubing carrier such that the tape sealing surface would be part of the gasket rather than the second tubing carrier.

Figure 10A:
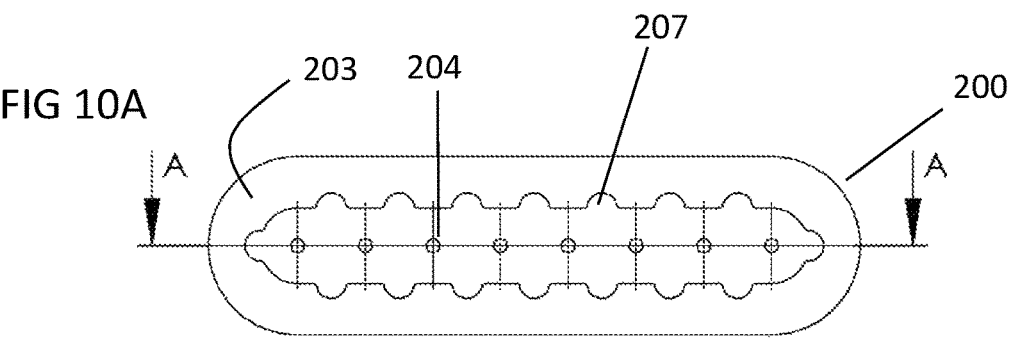
FIG. 10A shows a bottom view of FIG. 9.
Figure 10B:
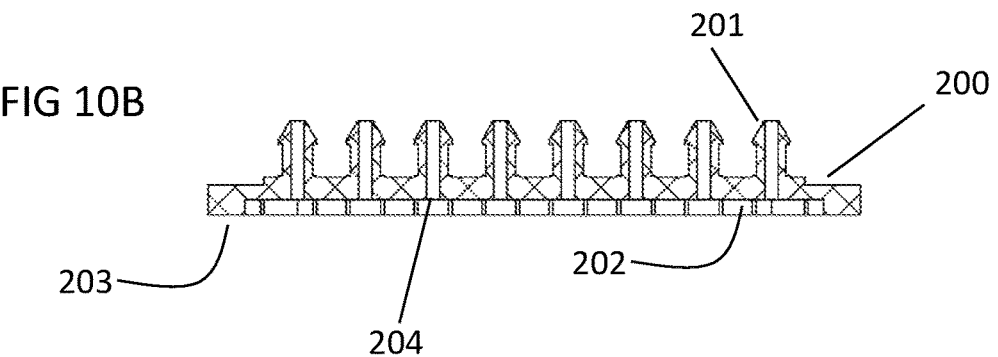
FIG. 10B shows a section view of FIG. 10A along the line A-A.

FIG. 10A shows a bottom view of the second tubing carrier 200 and FIG. 10B shows a section view along the line A-A in FIG. 10A. The cross section shows the fluidic connection between the fluid ports 201 and the openings 204 on the gasket sealing surface 202 of the first tubing carrier 200.

In further detail referring to FIGS. 9, 10A, and 10B, the second tubing carrier was fabricated by CNC machining 0.236 inch thick polycarbonate sheet stock to form the shape depicted in FIG. 5. The overall length was approximately 1.74 inches long and the width was approximately 0.48 inches wide. The tubing ports 201 were fabricated as tubing barbs were approximately 0.150 inches long, 0.10 inches in diameter at the widest point and an approximately 60 degree taper. The gasket pocket 206 was approximately 0.04 inches deep, but may be other depths determined by the thickness of the fluid sealing gasket 300, or may even be absent. The design principle is to ensure the fluid sealing gasket is not displaced when the tape sealing tabs are removed. This was accomplished with the gasket pocket in the described embodiment, but may also be accomplished using an adhesive or other bonding method to bond the gasket to the second gasket sealing surface 202. It should be noted that other fabrication methods may be used such as injection molding, 3D-printing, or other fabrication method. It should also be noted that the style of tubing port may vary, including cylindrical or other shaped tubing ports. It should also be noted that the overall dimensions may vary. It should also be noted that other materials may be used such as acrylic, polypropylene, cyclic-polyolefin-copolymer, or other plastic, or metal, or other material may be used.

Figure 11A:
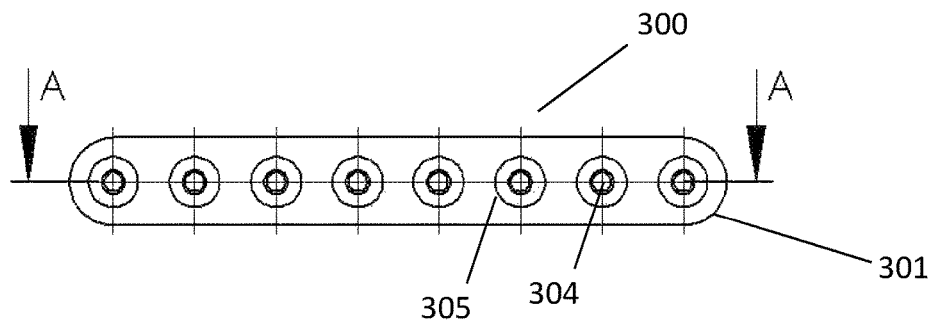
FIG. 11A is a top view of a fluid sealing gasket 300.

FIG. 11A is a top view of the fluid sealing gasket 300. The gasket comprises a fluid sealing gasket body 301, openings 304 corresponding to the openings 204 of the second tubing carrier, and seal ridges 305 around each gasket opening 304.

Figure 11B:
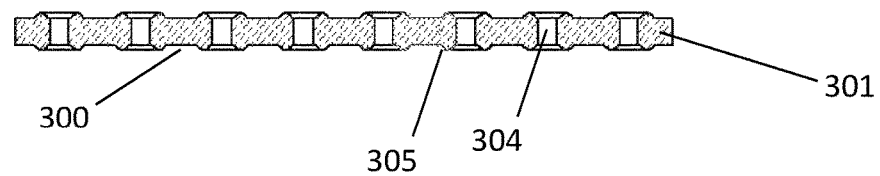
FIG. 11B is a section view of FIG. 11A along the line A-A.

FIG. 11B is a section view along the section line A-A of FIG. 11A. The fluid sealing gasket 300 was made from silicone by molding. It should be understood that the fluid sealing gasket 300 may be made from other suitable elastomeric or compressible materials. The length of the fluid sealing gasket 300 was approximately 1.45 inches long and 0.2 inches wide. The thickness of the fluid sealing gasket body 301 was 0.06 inches and the sealing ridges 305 were 0.01 inches high. It should be understood that other dimensions may be used. Design principles for selecting the dimensions of the gasket include choosing a gasket thickness such that the fluid sealing gasket will provide a "low pressure" seal when the connector is in an initial sealing configuration and can be further deformed to provide a final "high pressure" seal in a final sealing configuration.

Figure 12:
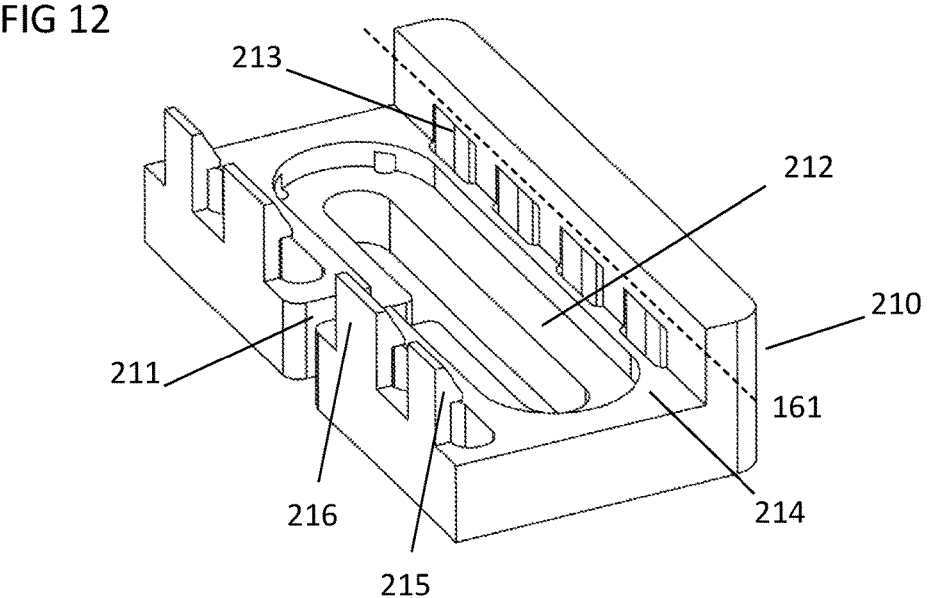
FIG. 12 is an isometric view of a second tubing carrier locking body 210.

FIG. 12 is an isometric view of the second tubing carrier locking body 210 which comprised a slot pocket 212 to mount the second tubing carrier 200 such that the tape sealing surface 203 was approximately flush with the cutout surface 214 of the second tubing carrier locking body 210; a hinge socket 213 in which a hinge claw 113 of the first tubing carrier locking body 110 was Inserted. A second tubing slot 211 to allow attachment of tubing to the second tubing carrier 200 prior to inserting the second tubing carrier 200 into the second tubing carrier locking body 210; a first snap-fit tab 215; and a second snap-fit tab 216. A preferred embodiment of snap-fit tabs had a 60 degree taper and approximately 0.05 to 0.06 inch deep undercut, 0.125 inches long undercut, approximately 0.05 to 0.06 thick undercut, and were approximately 0.175 and 0.26 inches wide. It should be understood that alternative dimensions may also be used. In particular thicker and wider tabs will provide more stiffness and resistance to the opening after snapping over a snap-fit tab ledge. The selection of the tab dimensions should be matched to the material properties of the second tubing carrier locking body 210 and the material and thickness of the fluid sealing gasket 300 so that the locking bodies 110, 210 are held in the proper position during the removal of the sealing tape tabs 120, 220.

Figure 13:
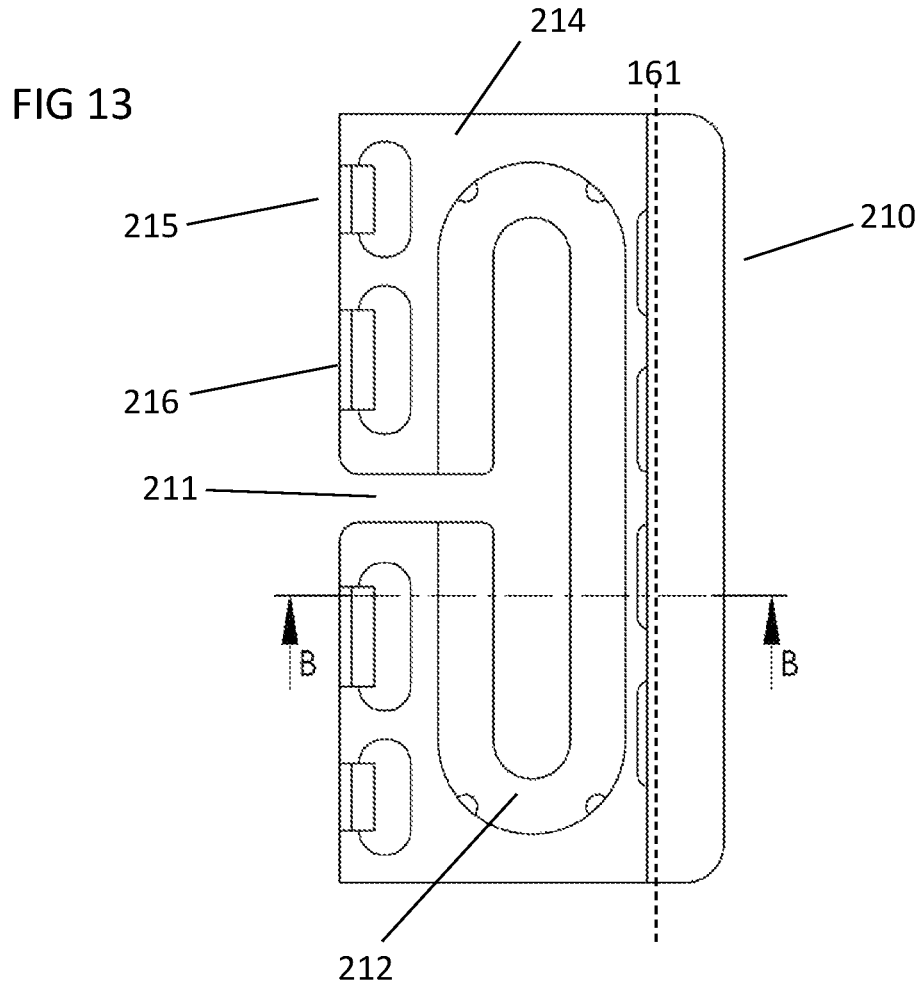
FIG. 13 is a top view of a second tubing carrier locking body 210.

FIG. 13 shows a top view of the second tubing carrier locking body. And FIG. 14 shows a section view along the line B-B of FIG. 13.

Figure 14:
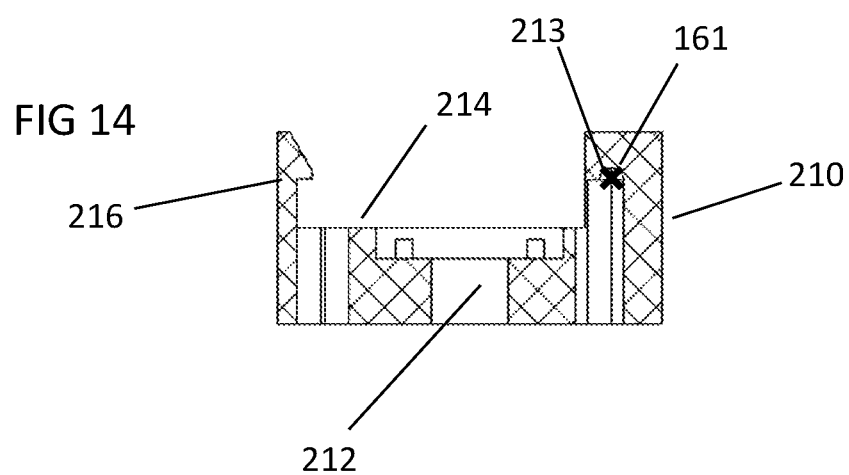
FIG. 14 a section view of FIG. 13 along the line B-B.

Referring to FIGS. 12, 13, 14 in more detail, the second tubing carrier locking body 210 was fabricated by CNC machining a 0.485 thick sheet of polycarbonate stock. The length of the second tubing carrier locking body 210 was 2.0 inches and the width was 1.0 inch. The distance between the top surface of the second tubing carrier locking body 210 and the cutout surface was 0.250 inches. It should be clear to one of ordinary skill in the art that the part could be fabricated using other materials, such as other thermoplastics, and also using other fabrication methods such as injection molding or 3D printing, or other fabrication methods.

Figure 15:
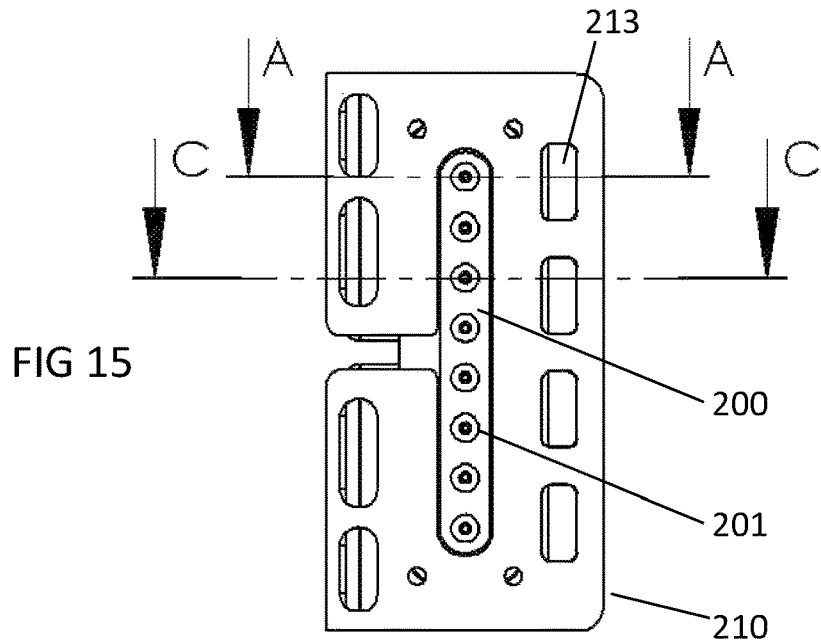
FIG. 15 is bottom view of an aseptic fluid connection assembly.

FIG. 15 shows a bottom view of an aseptic fluid connector embodiment. The sealing tape tabs 120, 220 are not shown. The section line A-A is for the section views shown in FIGS. 16A, 16B, 17A, and 17B. The section line C-C is for the section view shown in FIG. 17C. These section views illustrate the operation of the aseptic fluid connector. For clarity, tubing is not shown in FIGS. 15, 16A, 16B, 17A, 17B, and 17C. It should be understood that each half of the aseptic connector apparatus should be connected with tubing to two halves of a fluid system to be interconnected aseptically.

Figure 16A:
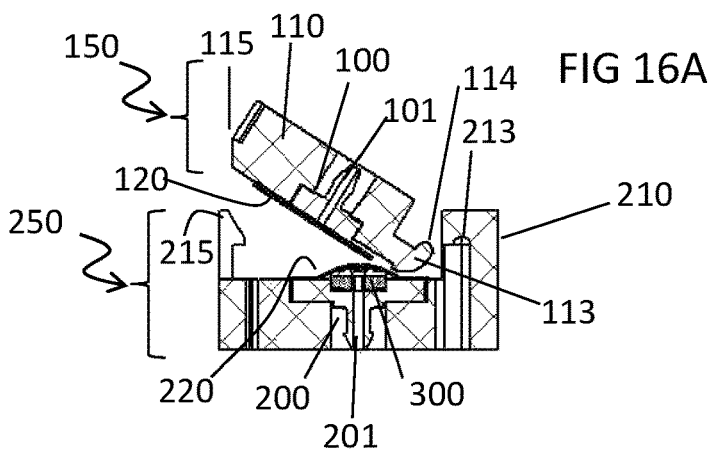
FIGS. 16A and 16B show section views of FIG. 15 along the line A-A showing the insertion of the first tubing carrier locking body 110 into the second tubing carrier locking body 210.

FIG. 16A shows a section view along the section line A-A of FIG. 15. In this configuration the first half 150 of the aseptic fluid connector apparatus was brought together with the second half 250 of the aseptic fluid connector apparatus at the angle depicted to enable the hinge claws 113 to enter the hinge sockets 213.

Figure 16B:
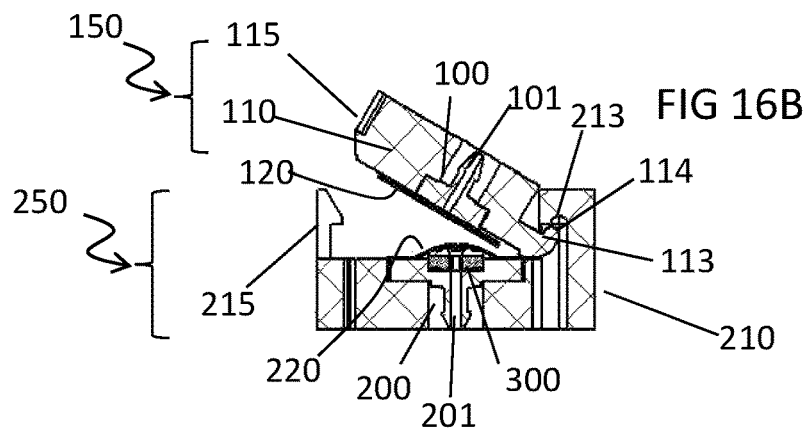

FIG. 16B shows the same section as FIG. 16A, in a configuration where the hinge claws 113 have entered the hinge sockets 213 but where the hinge claws 113 have not yet engaged the hinge sockets 213.

Figure 17A:
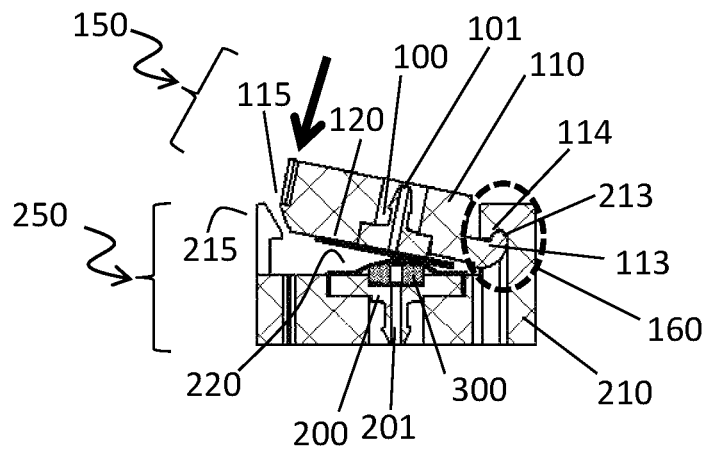
FIG. 17A is a section view of FIG. 15 along the line A-A showing the first tubing carrier locking body 110 in an open position with respect to the second tubing carrier locking body 210.
Figure 17B:
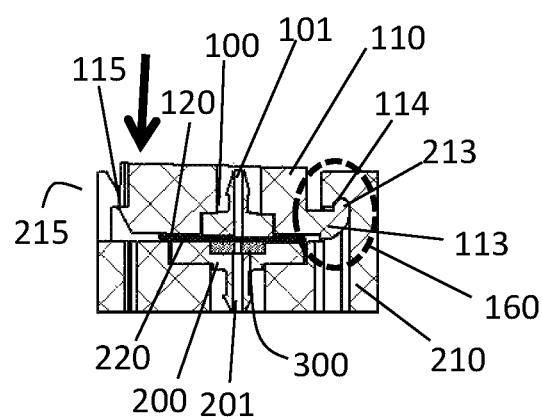
FIG. 17B is a section view of FIG. 15 along the line A-A showing the first tubing carrier locking body 110 in an initial sealing position with respect to the second tubing carrier locking body 210.
Figure 17C:
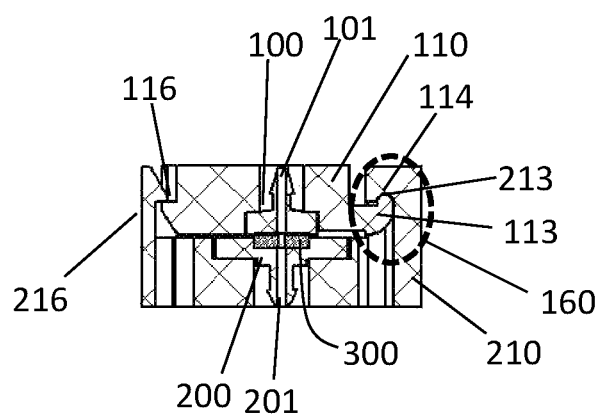
FIG. 17C is a section view of FIG. 15 along the line C-C showing the first tubing carrier locking body 110 in an final sealing position with respect to the second tubing carrier locking body 210.

FIG. 17A shows the same section as FIG. 16A with the hinge claws 113 engaged with the hinge sockets 213, forming a hinge coupling 160 indicated by the dashed ellipse, where the fluid sealing gasket 300 is in an uncompressed state. This configuration is called the open position. By applying a force at the area indicated by the thick arrow in FIG. 17A, the first half 150 of the aseptic fluid connector apparatus pivoted approximately at the cylindrical tip of the hinge claw 114 and the apparatus was brought into a condition of initial seal shown in FIG. 17B where the first snap-fit tab 215 had engaged with the first snap-fit tab ledge 115. In this condition, called the initial sealing position, the fluid sealing gasket 300 was in a first state of compression such that when the sealing tape tabs 120, 220 were removed, a low pressure, fluid tight seal was made between the ports 101 of the first tubing carrier 100 and the ports 201 of the second tubing carrier 200. In this condition, the sealing tape tabs 120, 220 were easily removed. After removing the sealing tape tabs 120, 220 additional force was applied at the area indicated by the thick arrow in FIG. 17B, which caused further pivoting, and some flexing of the first tubing carrier locking body 110 and second tubing carrier locking body 210 until the second snap-fit tabs 216 engaged the second snap-fit tab ledge 116. This condition is shown in FIG. 17C which is a section view along the line C-C in FIG. 15. In this final sealing position, the fluid sealing gasket 300 was in a state of higher compression than when in the initial sealing position and the fluid tight seal between the ports 101 of the first tubing carrier 100 and the ports 201 of the second tubing carrier 200 was improved and able to withstand higher pressures than when in the initial sealing position. Two different clamping positions, the initial sealing position and the final sealing position were used to facilitate the removal of the sealing tape tabs 120, 220. In the final sealing position, the pressure at the fluid sealing gasket 300 is high enough to make sealing tape tab 120, 220 removal very difficult and even fail by causing the sealing tape tabs 120, 220 to tear. For this reason an initial sealing position was used to provide a liquid tight seal to maintain sterility while allowing easy removal of the sealing tape tabs 120, 220. Providing an initial sealing position determined by engaging the first snap-fit tab 215 to the first snap-fit tab ledge 115 was important to indicate to the user sufficient compression of the fluid sealing gasket 300 had occurred before removing the sealing tape tabs 120, 220, and also to maintain the initial sealing position as the sealing tape tabs 120, 220 are removed.

Figure 18:
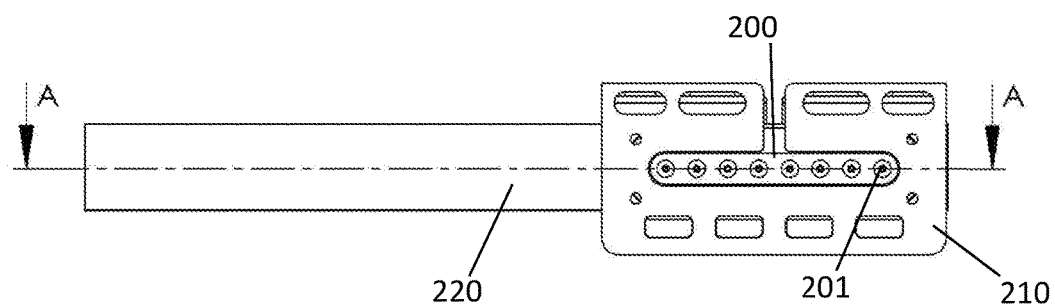
FIG. 18 is a bottom view of an aseptic fluid connection assembly.

FIG. 18 shows a bottom view of an aseptic fluid connector apparatus in the initial sealing position and a section line A-A.

Figure 19:
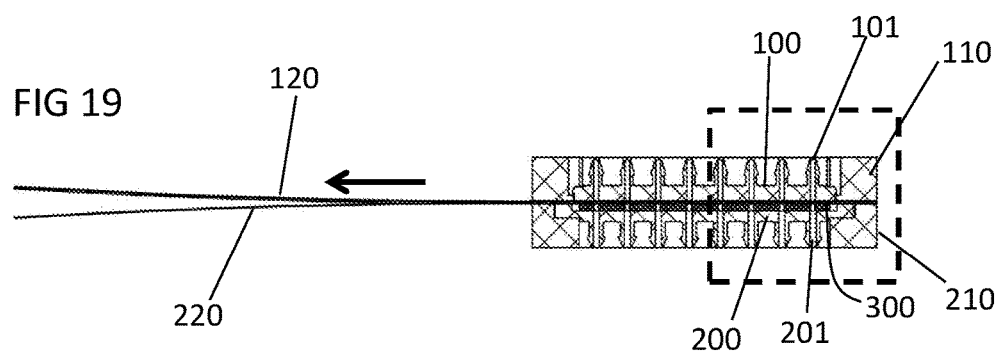
FIG. 19 is a section view of FIG. 18 along the line A-A.
Figure 20:
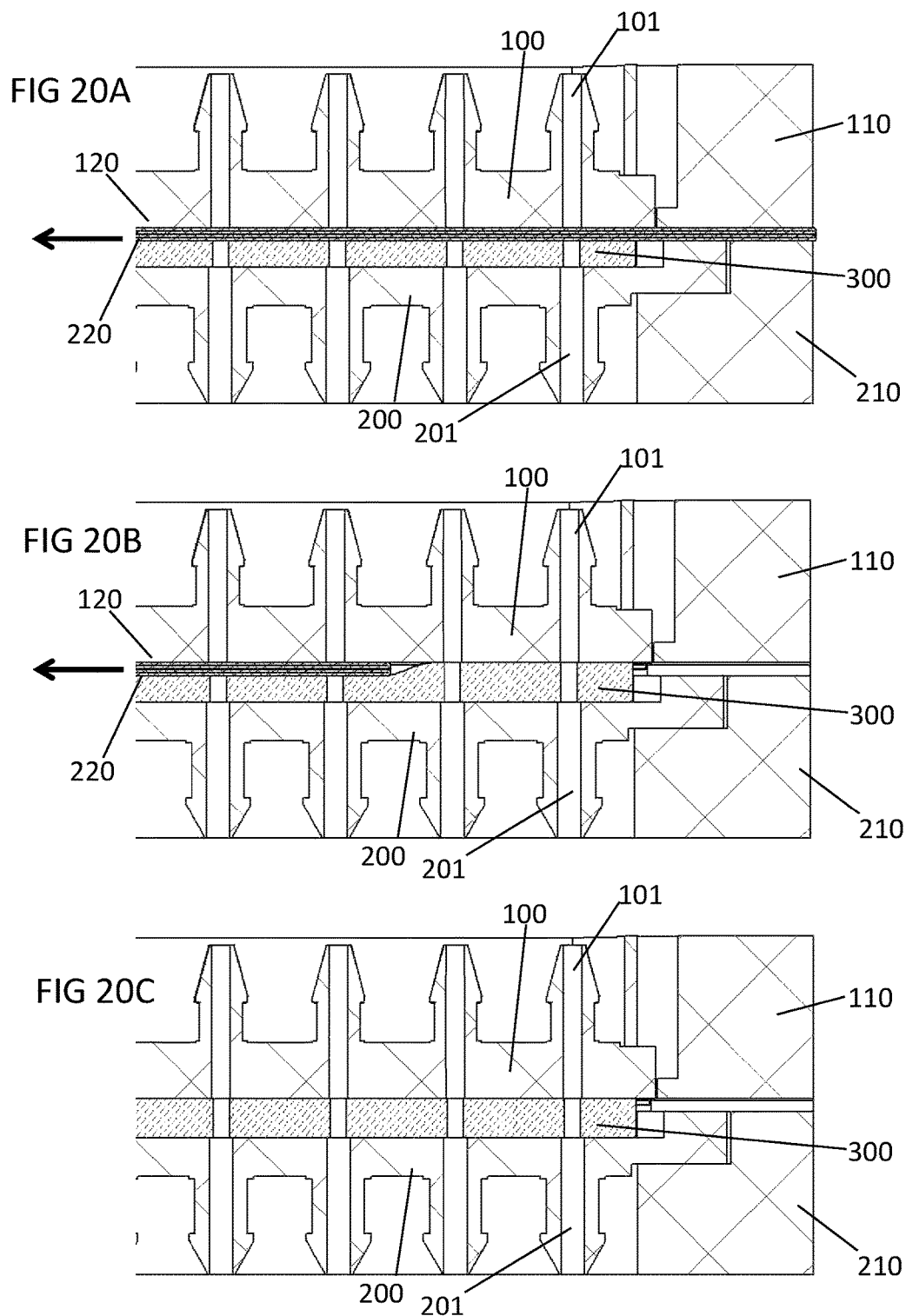
FIG. 20A is a zoomed view of the dashed region of FIG. 19 just before sealing tape tabs 120, 220 are pulled out.
FIG. 20B is a zoomed view of the dashed region of FIG. 19 showing the partial removal of sealing tape tabs 120, 220.
FIG. 20C is a zoomed view of the dashed region of FIG. 19 showing the sealing tape tabs removed.

FIG. 19 is a section view along the line A-A of FIG. 18. The arrow indicates the direction of pull for the sealing tape tabs 120, 220. The dashed rectangle shows the zoom area of FIGS. 20A, 20B, and 20C.

FIG. 20A shows the state just when the pulling on the sealing tape tabs 120, 220 begins. In this condition, the ports 101 of the first tubing carrier 100 and the ports 201 of the second tubing carrier 200 were sealed and isolated from each other and the fluid sealing gasket 300 was in a compressed state.

FIG. 20B shows the state where the sealing tape tabs 120, 220 had been pulled past two fluid ports 101, 201. The fluid sealing gasket 300, under compression, expanded into the space vacated by the sealing tape tabs 120, 220 to make an initial fluid tight seal that connected the first two ports 101 of the first tubing carrier 100 to the first two ports 201 of the second tubing carrier 200.

FIG. 20C shows the state where the sealing tape tabs 120, 220 had been removed and all ports 101 of the first tubing carrier 100 and all ports 201 of the second tubing carrier 200 remained in a state of initial seal. This tape removal process is analogous to U.S. Pat. No. 3,865,411 for a single aseptic connection.

Figure 21:
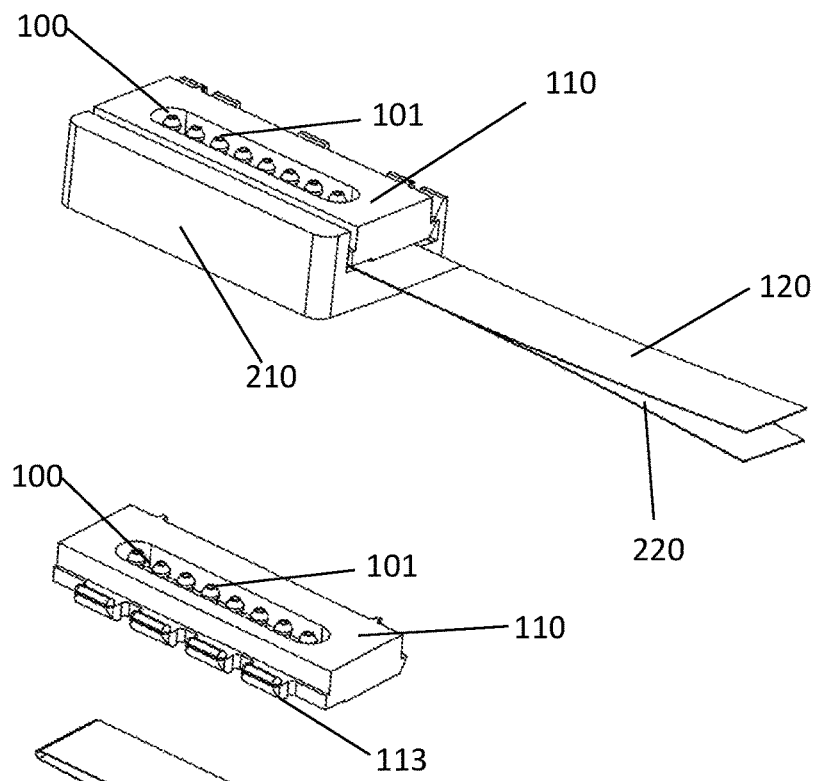
FIG. 21 is an isometric view of an alternative embodiment.
Figure 22:
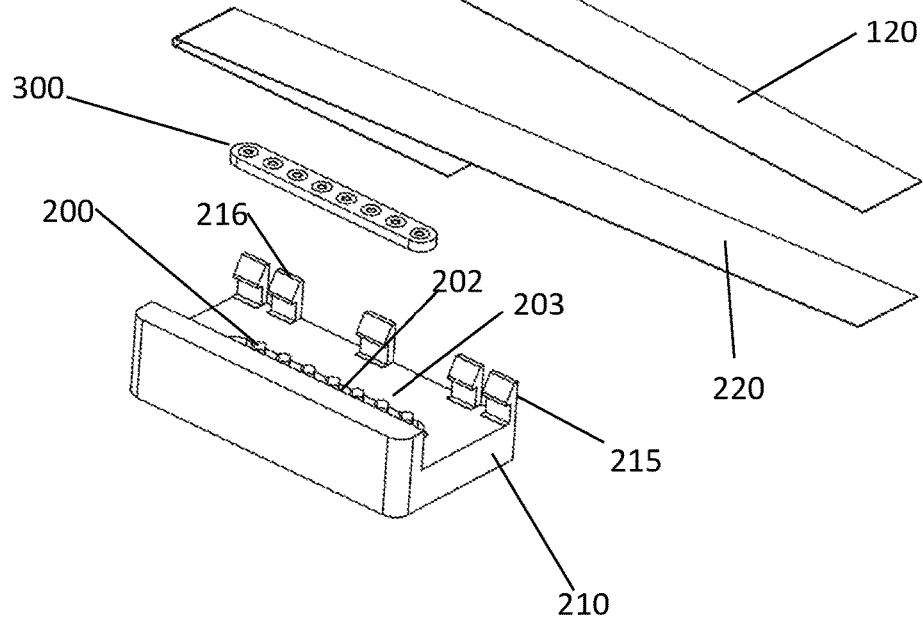
FIG. 22 is an exploded view of FIG. 21.

FIG. 21 and FIG. 22 show an embodiment of an aseptic fluid connector where the first tubing carrier 100 was integral to the first tubing carrier locking body 110 and where the second tubing carrier 200 was integral to the second tubing carrier locking body 210. This approach reduced the overall part count and simplified fabrication if using CNC machining, however this approach was not compatible with producing parts with injection molding.

Figure 23A:
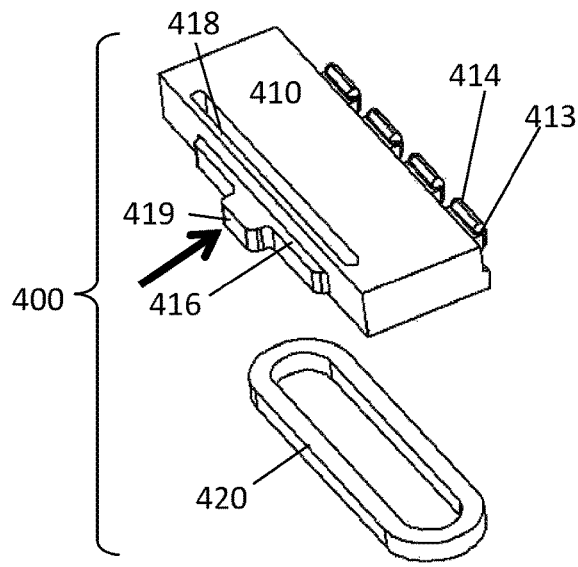
FIG. 23A shows a top isometric exploded view of a tape retention structure 400.
Figure 23B:
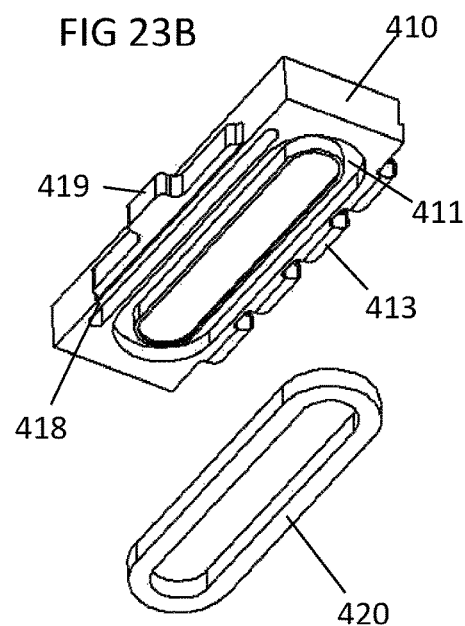
FIG. 23B shows a bottom isometric exploded view of a tape retention structure 400.
Figure 24:
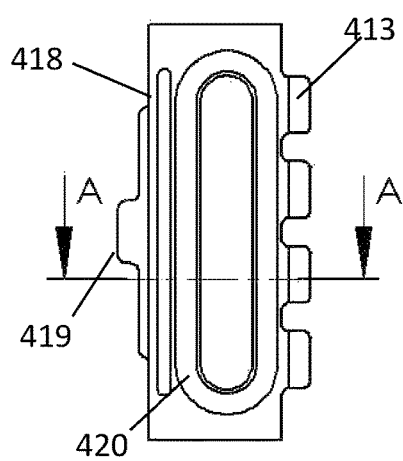
FIG. 24 shows a bottom view of a tape retention structure 400.
Figure 25:
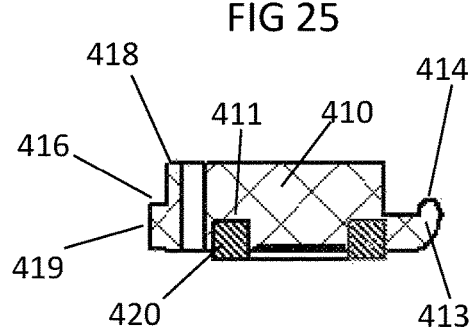
FIG. 25 shows a section view of FIG. 24 along the line A-A.

FIG. 23A and FIG. 23B show isometric views from the top and bottom of a tape retention structure 400. The tape retention structure comprised a tape retention structure body 410 having a tape retention gasket groove 411; a tape retention gasket 420; hinge claws 413; a snap-fit tab ledge 416 on a flexible member 418 with a flexible member push tab 419. Referring to FIG. 25 which is a section view along the line A-A of FIG. 24, when the tape retention gasket 420 was inserted into the tape retention gasket groove 411, approximately 0.02 inches of gasket protruded beyond the bottom face of the tape retention structure body 410. Therefore, when the tape retention structure 400 was inserted into the second tubing carrier locking body 210, analogous to the insertion and motion of the first tubing carrier locking body 110, and snapped closed such that the second snap-fit tabs 216 engaged the snap-fit tab ledge 416 on the flexible member 418, the tape retention gasket 420 applied pressure to the second sealing tape tab 220 to prevent it from peeling off inadvertently due to the distortion of the tape 220 from the bulging fluid sealing gasket 300 in the gasket pocket 206 of the second tubing carrier 200. When the tape retention structure 400 was engaged to the second snap-fit tabs 216, the fluid sealing gasket 300 was placed under a state of compression and the ports 201 of the second tubing carrier 200 were sealed and isolated to prevent any fluid leaks if pressure was applied in the tubing connected to the second tubing carrier 200. To release the tape retention structure, force was applied to the tape retention structure push tab 419, as shown by the thick arrow in FIG. 23A, which deformed the flexible member such that the snap-fit tab ledge 416 disengaged from the second snap-fit tabs 216 of the second tubing carrier locking body 210.

Referring in more detail to FIGS. 23A-25, the tape retention structure 400 was fabricated by CNC machining 0.236 inch thick polycarbonate sheet stock to form the shape depicted in FIG. 23A and FIG. 23B. The overall length was approximately 2 inches long and the width was approximately 0.9 inches wide. The flexible member was fabricated by machining a 0.0625 wide slot through the tape retention structure body 410, leaving an approximately 0.050 inch wide strip of material as the flexible member. It should be clear to one of ordinary skill in the art that the part could be fabricated using other materials, such as other thermoplastics, and also using other fabrication methods such as injection molding or 3D printing, or other fabrication methods.

EXAMPLE 1

Figure 26:
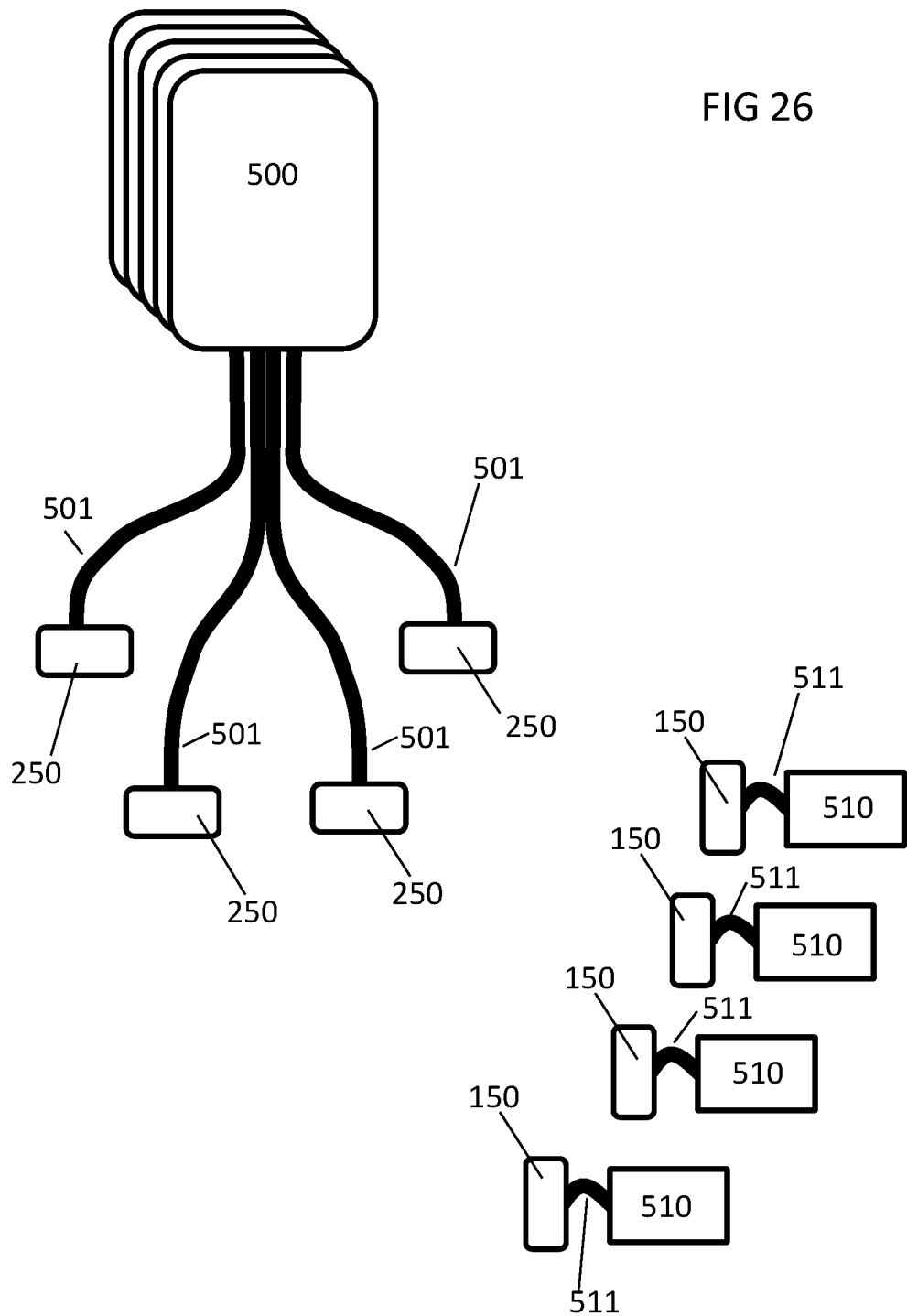
FIG. 26 shows a schematic representation of a set of fluid bags terminating in one half of the aseptic connector assembly 250 and a set of microfluidic devices terminating in another half of the aseptic connector assembly 150.

FIG. 26 shows a schematic representation of five fluid bags 500 connected to four second halves 250 of aseptic fluid connectors with a bundle of source tubing 501, and four first halves 150 of aseptic fluid connectors connected to four microfluidic devices 510 with a bundle of microfluidic device tubing 511. The entire bag assembly with aseptic connector halves are sterilized and the four microfluidic devices with aseptic connector halves are sterilized. When desired, the microfluidic devices 510 may be aseptically connected to the five bags 500 using the aseptic connector apparatus.

EXAMPLE 2

It should be noted that the dimensions and locations of the snap-fit tabs 215, 216 and the dimensions and locations of the snap-fit tab ledges 115, 116 need not be the positions and dimensions shown in the embodiment of FIGS. 1-20C. The dimensions and positions should be selected to provide an initial sealing position where: the sealing tape tabs 120, 220 may be reliably removed without excessive effort or tearing of the sealing tape tabs 120, 220, the initial sealing position is maintained during and after the removal of the sealing tape tabs 120, 220, and after removal of the sealing tape tabs 120,220, a fluid tight seal is maintained between the ports 101 of the first tubing carrier 100 and the ports 201 of the second tubing carrier 200; and a final sealing position where the fluid sealing gasket 300 is compressed sufficiently to so the seal between the ports 101 of the first tubing carrier 100 and the ports 201 of the second tubing carrier 200 withstand leakage against the desired pressure. It should be recognized by those of ordinary skill in the art that the appropriate dimensions of the snap-fit tabs 215, 216, snap-fit tab ledges 115, 116, the appropriate thickness of the fluid sealing gasket 300, the appropriate depth of the gasket pocket 206, and the thickness of the sealing tape tabs 120, 220 would depend on the material properties such as the elastic properties of the second tubing carrier locking body 210, the hardness and resiliency of the elastomeric material of the fluid sealing gasket 300.

Figure 27A:
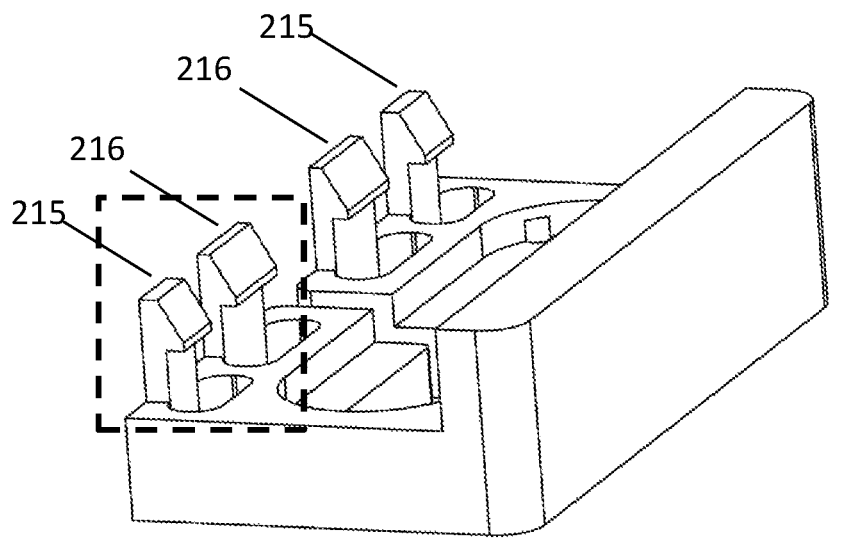
FIG. 27A shows an isometric view of a second tubing carrier locking body 210.
Figure 27B:
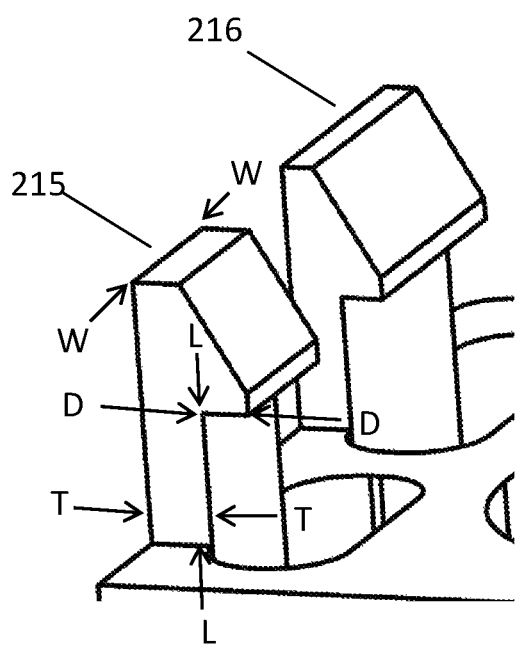
FIG. 27B is a zoomed view of FIG. 27A.
Figure 27C:
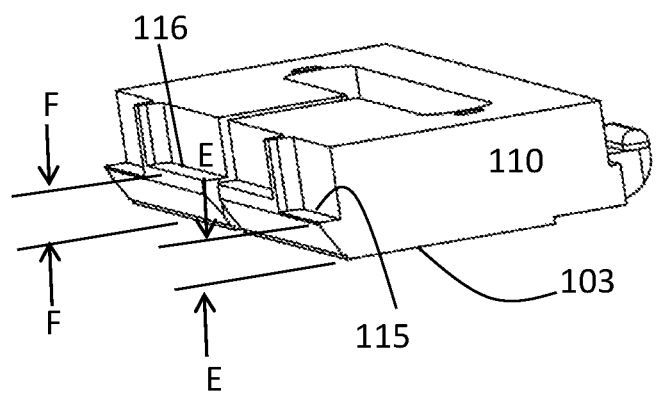
FIG. 27C shows an isometric view of a first tubing carrier locking body 110.

Referring to FIG. 27A, FIG. 27B, and FIG. 27C, an example preferred embodiment is shown, presenting details of important dimensions for the snap-fit tabs 215, 216 and snap-fit tab ledges 115, 116. In a preferred embodiment, the first snap-fit tabs 215 engaged the first snap-fit tab ledges 115 in the initial sealing position. In the initial sealing position, the bottom surface 103 of the first tubing carrier locking body 110 and the cutout surface 214 of the second tubing carrier locking body 210 were at an angle of approximately 2.11 degrees. Each sealing tape tab 120, 220 was folded over itself and therefore four layers of tape tab are present between the first tubing carrier locking body 110 and second tubing carrier locking body 210 in the initial sealing position. The combined thickness of the sealing tape tab layers and thickness of the fluid sealing gasket resulted in a relatively large force acting to push apart the first tubing carrier locking body 110 and second tubing carrier locking body 210. This force needed to be overcome by the force locking the first snap-fit tab 215 over the first snap-fit tab ledge 115. In addition, the act of pulling out the sealing tape tabs 120, 220 would sometimes result in an additional force acting to push apart the first tubing carrier locking body 110 and second tubing carrier locking body 210 if the tapes were not pulled in a direction purely along the plane of the sealing surface 214 of the second tubing carrier locking body 210. For these reasons, it was advantageous to increase the stiffness and locking depth of the first snap-fit tabs 215.

Referring to FIG. 27B, the dimensions indicated are W, the width of the snap-fit tab, L, the length of the undercut, T, the thickness of the undercut, and D, the depth of the undercut. For a preferred embodiment, W=0.175 inches, L=0.127 inches, T=0.06 inches, and D=0.045 inches. For comparison, the corresponding dimensions of the second snap-fit tabs 216 that are engaged to the second snap-fit tab ledges 116 were: W=0.260 inches, L=0.127 inches, T=0.05 inches, and D=0.03 inches.

Referring to FIG. 27C, the dimensions indicated are E, the distance between the first snap-fit ledge 115 and the bottom surface 103 of the first tubing carrier locking body 110 and F, the distance between the second snap-fit ledge 116 and the bottom surface 103 of the first tubing carrier locking body 110. For a preferred embodiment, E=0.090 inches and F=0.125 inches.

Definitions and Notes

"Approximately flush" shall refer to a condition two adjacent surfaces are within 0.03 inches of each other.

"fluid" refers to a liquid or a gas.

"low pressure" and "high pressure" refers to the relative pressure that the fluid tight seal between the ports 101 of the first tubing carrier 100, and the ports 201 of the second tubing carrier 200 can sustain without leaking. In other words, the pressure that can be sustained without leaking in the final sealing position is higher than the pressure that can be sustained in the initial sealing position. Example pressure ranges for "low pressure" are 0 psi to 1 psi, 0 psi to 3 psi, 0 psi to 5 psi, or 0 psi to 10 psi, or 0 psi to 15 psi, or other pressure ranges. Corresponding examples of "high pressure" would be >1 psi, >3 psi, >5 psi, >10 psi, or >15 psi, or greater than the upper end of a "low pressure" range. Although pressure ranges are described, the pressure ranges are not important, only that "high pressure" is higher than "low pressure".

"compression" or "state of compression" of the fluid sealing gasket 300 refers to an squeezing force applied to both sides of the fluid sealing gasket 300 by the first tubing carrier 100, and the second tubing carrier 200. When the gasket is preferably fabricated from an elastomeric material such as silicone, the fluid sealing gasket 300 is not compressible and does not technically compress, rather the fluid sealing gasket 300 deforms into the available space, such as the pocket cutouts 207. Potential mechanical energy is stored in the deformation of the fluid sealing gasket and results in a restoring force that tends to separate the first tubing carrier 100 and the second tubing carrier. When engaged, the snap-fit tabs 215, 216 and snap-fit tab ledges 115, 116 constrain the first tubing carrier 100 and second tubing carrier 200 so the fluid sealing gasket 300 remains in a deformed state and retains some mechanical potential energy.

"hinge coupling" refers to a mechanical structure that constrains the motion of two separable bodies to a rotation about an axis when the hinge coupling is engaged. In the context of the present invention, the hinge coupling comprises the hinge claws 113 on the first tubing carrier locking body 110 and the hinge sockets 213 on the second tubing carrier locking body 210. The hinge coupling ensures that the openings 104 of the first tubing ports 101 are aligned with the fluid sealing gasket openings 304 and openings 204 of the second tubing ports 201 when they are sealed in the initial and final sealing positions. Use of a hinge coupling for alignment is advantageous because there is only a single, unambiguous configuration to join the two separable bodies, and a single, unambiguous way to move the first tubing carrier locking body 110 into the initial sealing position and final sealing position. Although hinge-claws and hinge-sockets are preferred, other hinge couplings are contemplated such as a hinge pin with snap fit hinge claws, or a large hinge socket and a rounded over edge of the first tubing carrier locking body 110, or other hinge coupling.

"retaining structure" refers to a mechanical structure that constrains the rotation of two bodies between a first angle and a second angle. In the context of the present invention, a first retaining structure comprises the first snap-fit tab 215 and the first snap-fit tab ledge 115 that constrains the rotation of the first tubing carrier locking body 110 between an initial sealing position angle and a final sealing position angle when the first snap-fit tab 215 is engaged to the first snap-fit tab ledge 115. A second retaining structure comprises the second snap-fit tab 216 and the second snap-fit tab ledge 116 that constrains the rotation of the first tubing carrier locking body 110 to an angle less than the final sealing position angle when the second snap-fit tab 216 is engaged to the second snap-fit tab ledge 116. The angles referenced in this paragraph refer to the angle between the bottom surface 103 of the first tubing carrier locking body 110 and the cutout surface 214 of the second tubing carrier locking body 210. Use of the snap-fit tab 215, 216 and snap-fit tab ledge 115, 116 retaining structure is advantageous because combined with the hinge coupling and restoring force provided by the deformed fluid sealing gasket 300, the aseptic connector apparatus is simple to operate, with clear indications, from the snap click sound when the snap-fit tabs are engaged to the snap-fit tab ledges, when the initial and final sealing positions are reached. Although snap-fit tabs and snap-fit tab ledges are preferred, other retaining structures are contemplated, such as a bar with a locking cam having two positions, or a twist cam having two positions, or other retaining structure.

"adhered" refers to the a condition where the sealing tapes, or sealing films 120, 220 that are used to protect the first gasket sealing surface 102 and to protect the fluid sealing gasket 300 and second gasket sealing surface 202 from contamination, are temporarily bonded to the first gasket sealing surface 102 or the tape sealing surface 203. This may be through the use of an adhesive, such as a silicone pressure sensitive adhesive, or other adhesive, or with heat sealing, or other methods.

"integral" refers to the condition where features are formed in a single part.

Although the motivation for the present invention was for multiport aseptic interconnects, the inventive concepts may be applied to single port aseptic interconnects as well.

Although the overall dimensions of the aseptic fluid connector in the preferred embodiment are for generally small tubing with inner diameter approximately 0.0625 inches or less, the inventive concepts may be applied to larger tubing by scaling up the size of the physical structures and appropriately adjusting the size and position of the snap-fit tabs and snap-fit tab ledges, and adjusting the size and material of the fluid sealing gasket.

DRAWING LABEL LEGEND 100 first tubing carrier
101 individual tubing ports of first tubing carrier
102 gasket sealing surface
103 bottom surface of first tubing carrier locking body
104 openings of tubing ports
105 locking tab
110 first tubing carrier locking body
111 first tubing slot
112 slot pocket for first tubing carrier
113 hinge claw 114 cylindrical tip of hinge claw
115 first snap-fit tab ledge
116 second snap-fit tab ledge
120 first sealing tape tab
150 first half of aseptic fluid connector apparatus
160 hinge coupling
161 hinge coupling axis
200 second tubing carrier
201 individual tubing ports of second tubing carrier
202 gasket sealing surface
203 tape sealing surface
204 openings of tubing ports
206 gasket pocket
207 pocket cutouts
210 second tubing carrier locking body
211 second tubing slot
212 slot pocket for second tubing carrier
213 hinge socket
214 cutout surface
215 first snap-fit tab
216 second snap-fit tab
220 second sealing tape tab
250 second half of aseptic fluid connector apparatus
300 fluid sealing gasket
301 gasket body
304 gasket opening
305 seal ridges
400 tape retention structure
410 tape retention structure body
411 tape retention gasket groove
413 hinge claws
414 cylindrical tip of hinge claw
416 snap-fit tab ledge
418 flexible member
419 flexible member push tab
420 tape retention gasket
500 fluid source bags
501 source tubing bundle
510 microfluidic devices
511 microfluidic device tubing bundle Thus, specific compositions and methods of aseptic fluid interconnections have been disclosed. It should be apparent, however, to those skilled in the art that many more modifications besides those already described are possible without departing from the inventive concepts herein. The inventive subject matter, therefore, is not to be restricted except in the spirit of the disclosure.

Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An aseptic fluid connector apparatus comprising:
   a first tubing carrier comprising:
      a first gasket sealing surface with an opening;
      a first tubing port opposite the first gasket sealing surface, corresponding to the opening in the first gasket sealing surface;
   a first sealing tape tab adhered to the first gasket sealing surface;
   a second tubing carrier comprising:
      a second gasket sealing surface with an opening;
      a second tubing port opposite the second gasket sealing surface, corresponding to the opening in the second gasket sealing surface;
      a gasket retention pocket having gasket expansion regions; and
      a tape sealing surface;
   a fluid sealing gasket contacting the second gasket sealing surface, the fluid sealing gasket having an opening corresponding to the opening in the second gasket sealing surface;
   a second sealing tape tab covering the opening of the fluid sealing gasket;
   a clamping structure comprising:
      a first tubing carrier locking body that constrains the motion of the first tubing carrier;
      a second tubing carrier locking body that constrains the motion of the second tubing carrier;
      a hinge coupling, having an axis, between the first tubing carrier locking body and the second tubing carrier locking body;
      a first retaining structure; and
      a second retaining structure,
   Wherein the second sealing tape adheres to the tape sealing surface to protect the entire fluid sealing gasket from contamination,
   Wherein the hinge coupling between the first and second locking bodies constrains their movement such that the two locking bodies pivot along the hinge coupling axis between an open position, an initial sealing position, and a final sealing position, where in the open position the fluid sealing gasket is not compressed, in the initial sealing position the fluid sealing gasket is in a first state of compression such that there is a low pressure fluid tight seal between the first tubing port and the second tubing port, and in the final sealing position the fluid sealing gasket is further compressed in a second state of compression such that there is a high pressure fluid tight seal between the first tubing port and the second tubing port,
   Wherein the first retaining structure constrains the locking bodies from moving from the initial sealing position to the open position, and the second retaining structure constrains the locking bodies in the final sealing position.

2. An aseptic fluid connector apparatus comprising:
   a first tubing carrier comprising:
      a first gasket sealing surface with an opening;
      a first tubing port opposite the first gasket sealing surface, corresponding to the opening in the first gasket sealing surface;
   a first sealing tape tab adhered to the first gasket sealing surface;
   a second tubing carrier comprising:
      a second gasket sealing surface with an opening;
      a second tubing port opposite the second gasket sealing surface, corresponding to the opening in the second gasket sealing surface;
   a fluid sealing gasket contacting the second gasket sealing surface, the fluid sealing gasket having an opening corresponding to the opening in the second gasket sealing surface;
   a second sealing tape tab covering the opening of the fluid sealing gasket;
   a clamping structure comprising:
      a first tubing carrier locking body that constrains the motion of the first tubing carrier;
      a second tubing carrier locking body that constrains the motion of the second tubing carrier;

a hinge coupling, having an axis, between the first tubing carrier locking body and the second tubing carrier locking body;
a first retaining structure; and
a second retaining structure,
Wherein the hinge coupling between the first and second locking bodies constrains their movement such that the two locking bodies pivot along the hinge coupling axis between an open position, an initial sealing position, and a final sealing position, where in the open position the fluid sealing gasket is not compressed, in the initial sealing position the fluid sealing gasket is in a first state of compression such that there is a low pressure fluid tight seal between the first tubing port and the second tubing port, and in the final sealing position the fluid sealing gasket is further compressed in a second state of compression such that there is a high pressure fluid tight seal between the first tubing port and the second tubing port,
Wherein the first retaining structure constrains the locking bodies from moving from the initial sealing position to the open position, and the second retaining structure constrains the locking bodies in the final sealing position,
Wherein the hinge coupling comprises a first half that is integral to the first tubing carrier locking body and a second half that is integral to the second tubing carrier locking body, where the first half of the hinge coupling comprises a set of claws and the second half of the hinge coupling comprises a set of sockets.

3. The apparatus of claim 2 where the first tubing carrier and the first tubing carrier locking body are integral.

4. The apparatus of claim 2 where the second tubing carrier and the second tubing carrier locking body are integral.

5. The apparatus of claim 2 further comprising
a tape retention structure comprising a tape retention structure body that is used to maintain the seal of the second tape tab to the second tubing carrier before the aseptic connector apparatus is used; and
a tape retention hinge coupling between the tape retention structure and the second tubing carrier locking body,
Wherein the tape retention hinge coupling comprises a first half that is integral to the tape retention structure body and a second half that is integral to the second tubing carrier locking body and the first half of the tape retention hinge coupling comprises a set of claws and the second half of the tape retention hinge coupling comprises a set of sockets.

6. An aseptic fluid connector apparatus comprising:
a first tubing carrier comprising:
a first gasket sealing surface with an opening;
a first tubing port opposite the first gasket sealing surface, corresponding to the opening in the first gasket sealing surface;
a first sealing tape tab adhered to the first gasket sealing surface;
a second tubing carrier comprising:
a second gasket sealing surface with an opening;
a second tubing port opposite the second gasket sealing surface, corresponding to the opening in the second gasket sealing surface;
a fluid sealing gasket contacting the second gasket sealing surface, the fluid sealing gasket having an opening corresponding to the opening in the second gasket sealing surface;
a second sealing tape tab covering the opening of the fluid sealing gasket;
a clamping structure comprising:
a first tubing carrier locking body that constrains the motion of the first tubing carrier comprising:
a first snap-fit tab ledge;
a second snap-fit tab ledge;
a second tubing carrier locking body that constrains the motion of the second tubing carrier;
a hinge coupling, having an axis, between the first tubing carrier locking body and the second tubing carrier locking body;
a first retaining structure comprising:
a first snap-fit locking tab integral to the second tubing carrier locking body; and
a second retaining structure comprising:
a second snap-fit locking tab integral to the second tubing carrier locking body,
Wherein the hinge coupling between the first and second locking bodies constrains their movement such that the two locking bodies pivot along the hinge coupling axis between an open position, an initial sealing position, and a final sealing position, where in the open position the fluid sealing gasket is not compressed, in the initial sealing position the fluid sealing gasket is in a first state of compression such that there is a low pressure fluid tight seal between the first tubing port and the second tubing port, and in the final sealing position the fluid sealing gasket is further compressed in a second state of compression such that there is a high pressure fluid tight seal between the first tubing port and the second tubing port,
Wherein the first retaining structure constrains the locking bodies from moving from the initial sealing position to the open position, and the second retaining structure constrains the locking bodies in the final sealing position,
Where in the initial sealing position, the first snap-fit locking tab is engaged to the first snap-fit tab ledge on the first tubing carrier locking body; and in the final sealing position, the second snap-fit locking tab is engaged to the second snap-fit tab ledge on the first tubing carrier locking body and the first snap-fit locking tab is no longer engaged to the first snap-fit tab ledge on the first tubing carrier locking body.

* * * * *